(12) United States Patent
Nair et al.

(10) Patent No.: US 9,005,475 B2
(45) Date of Patent: *Apr. 14, 2015

(54) AROMATIC AMIDE COMPOUND

(71) Applicant: Ticona LLC, Florence, KY (US)

(72) Inventors: Kamlesh P. Nair, Florence, KY (US); Steven D. Gray, Mequon, WI (US)

(73) Assignee: Ticona LLC, Florence, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/296,492

(22) Filed: Jun. 5, 2014

(65) Prior Publication Data
US 2014/0288221 A1  Sep. 25, 2014

Related U.S. Application Data

(63) Continuation of application No. 13/594,916, filed on Aug. 27, 2012, now Pat. No. 8,778,221.

(60) Provisional application No. 61/528,445, filed on Aug. 29, 2011, provisional application No. 61/664,911, filed on Jun. 27, 2012.

(51) Int. Cl.
| | |
|---|---|
| *C09K 19/38* | (2006.01) |
| *C08G 63/02* | (2006.01) |
| *C08G 64/00* | (2006.01) |
| *C07C 233/80* | (2006.01) |
| *C09K 19/22* | (2006.01) |
| *C09K 19/54* | (2006.01) |
| *C08L 77/12* | (2006.01) |
| *C08K 5/20* | (2006.01) |
| *C07C 231/02* | (2006.01) |
| *C09K 19/04* | (2006.01) |

(52) U.S. Cl.
CPC ............ *C07C 233/80* (2013.01); *C09K 19/22* (2013.01); *C09K 19/38* (2013.01); *C09K 19/54* (2013.01); *C08L 77/12* (2013.01); *C09K 2019/0481* (2013.01); *C08K 5/20* (2013.01); *C07C 231/02* (2013.01)

(58) Field of Classification Search
USPC ............ 564/142, 153, 155, 156; 252/299.01, 252/299.5; 528/190, 193; 526/306, 307.2
See application file for complete search history.

(56) References Cited

U.S. PATENT DOCUMENTS

| | | | |
|---|---|---|---|
| 4,002,600 A | 1/1977 | Habermeier | |
| 4,038,416 A | 7/1977 | Mori et al. | |
| 4,083,829 A | 4/1978 | Calundann et al. | |
| 4,132,840 A | 1/1979 | Hugl et al. | |
| 4,161,470 A | 7/1979 | Calundann et al. | |
| 4,163,099 A | 7/1979 | Buxbaum et al. | |
| 4,184,996 A | 1/1980 | Calundann | |
| 4,219,461 A | 8/1980 | Calundann | |
| 4,256,624 A | 3/1981 | Calundann | |
| 4,279,803 A | 7/1981 | Calundann | |
| 4,318,841 A | 3/1982 | East et al. | |
| 4,330,457 A | 5/1982 | East et al. | |
| 4,330,668 A | 5/1982 | Hideo et al. | |
| 4,337,190 A | 6/1982 | Calundann | |
| 4,339,375 A | 7/1982 | Calundann et al. | |
| 4,351,917 A | 9/1982 | Calundann et al. | |
| 4,351,918 A | 9/1982 | Charbonneau et al. | |
| 4,355,132 A | 10/1982 | East et al. | |
| 4,355,134 A | 10/1982 | Charbonneau et al. | |

(Continued)

FOREIGN PATENT DOCUMENTS

| | | |
|---|---|---|
| EP | 0 055 480 | 7/1982 |
| EP | 0 071 968 | 2/1983 |

(Continued)

OTHER PUBLICATIONS

CAPLUS 1973:442940.*
Abstract of German Patent—DE2041773, 1972, 1 page.
Abstract of German Patent—DE4017685, Dec. 5, 1991, 1 page.
Abstract of European Patent—EP0523326, Jan. 20, 1993, 1 page.
Abstract of Japanese Patent—JPS5861145, Apr. 12, 1983, 1 page.
Abstract of Japanese Patent—JPS5861146, Apr. 12, 1983, 1 pages.
Abstract of Japanese Patent—JPS5883048, May 18, 1983, 2 pages.
Abstract of Japanese Patent—JPS5893718, Jun. 3, 1983, 2 pages.

(Continued)

*Primary Examiner* — Shean C Wu
(74) *Attorney, Agent, or Firm* — Dority & Manning, P.A.

(57) ABSTRACT

An aromatic amide compound having the following general formula (I) is provided:

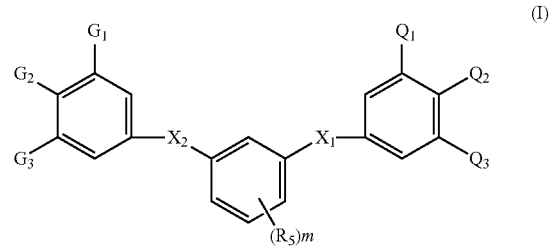

wherein,
  $X_1$ and $X_2$ are independently C(O)HN or NHC(O);
  $G_1$, $G_2$ and $G_3$ are independently hydrogen, C(O)HN-phenyl, or NHC(O)-phenyl, wherein at least one of $G_1$, $G_2$ and $G_3$ is C(O)HN-phenyl or NHC(O)-phenyl;
  $Q_1$, $Q_2$, and $Q_3$ are independently hydrogen, C(O)HN-phenyl, or NHC(O)-phenyl, wherein at least one of $Q_1$, $Q_2$, and $Q_3$ is C(O)HN-phenyl or NHC(O)-phenyl;
  $R_5$ is halo, haloalkyl, alkyl, alkenyl, aryl, heteroaryl, cycloalkyl, or heterocyclyl; and
  m is from 0 to 4.

15 Claims, 2 Drawing Sheets

(56) References Cited

U.S. PATENT DOCUMENTS

| | | |
|---|---|---|
| 4,375,530 A | 3/1983 | Hay et al. |
| 4,387,210 A | 6/1983 | Katoh et al. |
| 4,393,191 A | 7/1983 | East |
| 4,421,908 A | 12/1983 | East |
| 4,429,105 A | 1/1984 | Charbonneau |
| 4,434,262 A | 2/1984 | Buckley et al. |
| 4,473,682 A | 9/1984 | Calundann et al. |
| 4,511,709 A | 4/1985 | Yoo et al. |
| 4,522,974 A | 6/1985 | Calundann et al. |
| 4,563,508 A | 1/1986 | Cottis et al. |
| 4,581,399 A | 4/1986 | Yoon |
| 4,611,025 A | 9/1986 | Akkapeddi et al. |
| 4,650,836 A | 3/1987 | George et al. |
| 4,778,858 A | 10/1988 | Ginnings |
| 4,831,104 A | 5/1989 | Aya et al. |
| 4,851,562 A | 7/1989 | de Jonge et al. |
| 4,904,752 A | 2/1990 | Kanoe et al. |
| 4,952,662 A | 8/1990 | Finke et al. |
| 4,968,737 A | 11/1990 | Finke et al. |
| 4,980,444 A | 12/1990 | de Jonge et al. |
| 4,980,504 A | 12/1990 | de Jonge et al. |
| 5,093,464 A | 3/1992 | Yoon et al. |
| 5,102,935 A | 4/1992 | Heinz et al. |
| 5,120,820 A | 6/1992 | Fujiwara et al. |
| 5,162,489 A | 11/1992 | de Jonge et al. |
| 5,171,823 A | 12/1992 | Charbonneau et al. |
| 5,204,443 A | 4/1993 | Lee et al. |
| 5,221,730 A | 6/1993 | Morris et al. |
| 5,237,038 A | 8/1993 | Morris et al. |
| 5,258,470 A | 11/1993 | Poll et al. |
| 5,271,865 A | 12/1993 | Hittich et al. |
| 5,298,593 A | 3/1994 | Fujiwara et al. |
| 5,324,795 A | 6/1994 | Suenaga |
| 5,334,343 A | 8/1994 | Po' et al. |
| 5,352,746 A | 10/1994 | Asai et al. |
| 5,446,124 A | 8/1995 | Niwano et al. |
| 5,480,907 A | 1/1996 | Hayashi et al. |
| 5,496,893 A | 3/1996 | Gagné et al. |
| 5,500,294 A | 3/1996 | Sakumoto et al. |
| 5,510,189 A | 4/1996 | Sakumoto et al. |
| 5,534,187 A | 7/1996 | Miyazawa et al. |
| 5,541,240 A | 7/1996 | Makhija et al. |
| 5,541,267 A | 7/1996 | Akkapeddi et al. |
| 5,563,216 A | 10/1996 | Niwano et al. |
| 5,573,752 A | 11/1996 | Ranganathan et al. |
| 5,609,956 A | 3/1997 | Sakumoto et al. |
| 5,614,316 A | 3/1997 | Hashimoto et al. |
| 5,616,680 A | 4/1997 | Linstid, III |
| 5,766,507 A | 6/1998 | Nakai |
| 5,779,936 A | 7/1998 | Miyasawa et al. |
| 5,976,406 A | 11/1999 | Nagano et al. |
| 5,997,765 A | 12/1999 | Furuta et al. |
| 6,114,492 A | 9/2000 | Linstid, III et al. |
| 6,294,618 B1 | 9/2001 | Soelch |
| 6,312,772 B1 | 11/2001 | Kuder et al. |
| 6,376,076 B1 | 4/2002 | Ohbe et al. |
| 6,498,274 B1 | 12/2002 | Brown et al. |
| 6,514,611 B1 | 2/2003 | Shepherd et al. |
| 6,613,847 B2 | 9/2003 | Soelch |
| 6,649,730 B2 | 11/2003 | Okamoto et al. |
| 6,656,386 B2 | 12/2003 | Suenaga et al. |
| 6,680,002 B2 | 1/2004 | Yamauchi et al. |
| 6,702,956 B2 | 3/2004 | Maeda et al. |
| 6,740,728 B2 | 5/2004 | Ding et al. |
| 6,755,992 B2 | 6/2004 | Okamoto et al. |
| 7,179,401 B2 | 2/2007 | Ueno et al. |
| 7,238,714 B2 | 7/2007 | Nakao et al. |
| 7,335,318 B2 | 2/2008 | Asahara et al. |
| 7,343,675 B2 | 3/2008 | Smith et al. |
| 7,344,657 B2 | 3/2008 | Okamoto et al. |
| 7,393,467 B2 | 7/2008 | Asahara et al. |
| 7,405,250 B2 | 7/2008 | Kim |
| 7,507,784 B2 | 3/2009 | Dingemans et al. |
| 7,534,914 B2 | 5/2009 | Koike et al. |
| 7,592,413 B2 | 9/2009 | Citron et al. |
| 7,648,748 B2 | 1/2010 | Nakane et al. |
| 7,754,717 B2 | 7/2010 | Dimauro et al. |
| 7,759,344 B2 | 7/2010 | Booker et al. |
| 7,790,793 B2 | 9/2010 | Schmidt et al. |
| 7,795,315 B2 | 9/2010 | Chen et al. |
| 7,803,307 B2 | 9/2010 | Zimmerman |
| 7,824,572 B2 | 11/2010 | Okamoto |
| 7,825,176 B2 | 11/2010 | Kim et al. |
| 8,034,255 B2 | 10/2011 | Goldfinger |
| 8,084,476 B2 | 12/2011 | Koike et al. |
| 8,084,637 B2 | 12/2011 | Chopra et al. |
| 8,142,683 B2 | 3/2012 | Murouchi et al. |
| 8,309,734 B2 | 11/2012 | Bissantz et al. |
| 8,778,221 B2 * | 7/2014 | Nair et al. ............ 252/299.01 |
| 2004/0135118 A1 | 7/2004 | Waggoner |
| 2006/0019110 A1 | 1/2006 | Sato et al. |
| 2006/0073306 A1 | 4/2006 | Nakane et al. |
| 2007/0106035 A1 | 5/2007 | Gomurashvili et al. |
| 2007/0185118 A1 | 8/2007 | Hooft Van Huijsduijnene et al. |
| 2007/0232594 A1 | 10/2007 | Yokoyama et al. |
| 2009/0001317 A1 | 1/2009 | Okamoto |
| 2009/0111950 A1 | 4/2009 | Yamazaki et al. |
| 2009/0275697 A1 | 11/2009 | Waggoner et al. |
| 2010/0130743 A1 | 5/2010 | Wada et al. |
| 2011/0071304 A1 | 3/2011 | Fujimaki et al. |
| 2011/0184188 A1 | 7/2011 | Wada et al. |
| 2012/0022202 A1 | 1/2012 | Suh et al. |
| 2013/0048908 A1 | 2/2013 | Gray et al. |
| 2013/0048909 A1 | 2/2013 | Nair et al. |
| 2013/0048910 A1 | 2/2013 | Nair et al. |
| 2013/0048914 A1 | 2/2013 | Nair et al. |
| 2013/0053531 A1 | 2/2013 | Nair et al. |
| 2013/0053532 A1 | 2/2013 | Nair et al. |
| 2013/0053533 A1 | 2/2013 | Nair et al. |

FOREIGN PATENT DOCUMENTS

| | | |
|---|---|---|
| EP | 0 376 615 | 7/1990 |
| EP | 0 396 955 | 11/1990 |
| EP | 0 413 375 | 2/1991 |
| EP | 0 450 652 | 10/1991 |
| EP | 0 569 980 | 11/1993 |
| EP | 0 852 249 | 7/1998 |
| EP | 1 095 930 | 5/2001 |
| EP | 1 792 942 | 6/2007 |
| GB | 2 158 832 | 11/1985 |
| WO | WO 95/33803 | 12/1995 |
| WO | WO 98/22103 | 5/1998 |
| WO | WO 2004/058851 | 7/2004 |
| WO | WO 2007/038373 | 4/2007 |

OTHER PUBLICATIONS

Abstract of Japanese Patent—JPS58219233, Dec. 20, 1983, 2 pages.
Abstract of Japanese Patent—JPS6049026, Mar. 18, 1984, 2 pages.
Abstract of Japanese Patent—JPS59196364, Nov. 7, 1984, 1 page.
Abstract of Japanese Patent—JPS63137950, Jun. 9, 1988, 1 page.
Abstract of Japanese Patent—JPS63280730, No. 17, 1988, 2 pages.
Abstract of Japanese Patent—JPS63280731, Nov. 17, 1988, 1 page.
Abstract of Japanese Patent—JPS63280732, Nov. 17, 1988, 2 pages.
Abstract of Japanese Patent—JPH01115926, May 9, 1989, 1 page.
Abstract of Japanese Patent—JPH02151626, Jun. 11, 1990, 1 page.
Abstract of Japanese Patent—JPH02240134, Sep. 25, 1990, 1 page.
Abstract of Japanese Patent—JPH02240138, Sep. 25, 1990, 1 page.
Abstract of Japanese Patent—JPH03072559, Mar. 27, 1991, 1 page.
Abstract of Japanese Patent—JPH03095260, Apr. 19, 1991, 2 pages.
Abstract of Japanese Patent—JPH0673239, Mar. 15, 1994, 1 page.
Abstract of Japanese Patent—JPH06347770A, Dec. 22, 1994, 2 pages.
Abstract of Japanese Patent—JPH09143347A, Jun. 3, 1997, 1 page.
Abstract of Japanese Patent—JPH09249813A, Sep. 22, 1997, 2 pages.
Abstract of Japanese Patent—JPH1160927A, Mar. 5, 1999, 2 pages.
Abstract of Japanese Patent—JP2004182748A, Jul. 2, 2004, 1 page.
Abstract of Japanese Patent—JP2005248052A, Sep. 15, 2005, 1 page.
Abstract of Japanese Patent—JP2005298772A, Oct. 27, 2005, 1 page.

(56) References Cited

OTHER PUBLICATIONS

Abstract of Japanese Patent—JP2006225644, Aug. 31, 2006, 1 page.
Abstract of Japanese Patent—JP2006257047, Sep. 28, 2006, 1 page.
Abstract of Japanese Patent—JP2007238851A, Sep. 20, 2007, 1 page.
Abstract of Japanese Patent—JP2009108179A, May 21, 2009, 1 page.
Abstmct of japanese Patent—JP2009108180A, May 21, 2009, 1 page.
Abstract of Japanese Patent—JP2010174114A, Aug. 12, 2010, 1 page.
Abstract of Polish Patent—PL92807, 1977, 1 page.
Abstract of Taiwanese Patent—TW397859B. Jul. 11, 2000, 1 page.
Article—Han et al., "A Change in Mechanism from Acidolysis to Phenolysis in the Bulk Copolymerization of 4-Acetoxybenzoic Acid and 6-Acetoxy-2-naphthoic Acid," *Macromolecules*, 1996, vol. 29, No. 26, pp. 8313-8320.
Article—Gale et al., "Conformational Control of Selectivity and Stability in Hybrid Amide/Urea Macrocycles," *Chem. Eur. J.*, vol. 13, 2007, pp. 3320-3329.
Abstract of Article—Ueda et al., "Diphenyl (2,3-Dihydro-2-thioxo-3-benzoxazolyl)phosphonate: A New, Reactive Activating Agent for the Synthesis of Amides and Polyamides," *Macromolecules*, vol. 21, No. 1, 1988, pp. 19-24.
Article—Washio et al , "Facile Synthesis of Polyamide Dendrimers from Unprotected $AB_2$ Building Blocks: Dumbbell-Shaped Dendrimer, Star-Shaped Dendrimer, and Dendrimer with a Carboxylic Acid at the Core," *Macromolecules*, vol. 38, No. 6, 2005, pp. 2237-2246.
Article—Kuz'min et al., "Kinetics of Acylation of Anilines Monosubstituted in the Ring by Benzoyl Chloride in N, N-Dimethylacetamide," *Zhurnal Organicheskoi Khimii*, vol. 17, No. 11, pp. 2394-2396, 1981.
Abstract of Article—Sokolova et al., "Physicochemical Studies of Individual Aromatic Oligoamides," Caplus, vol. 15, No. 3, 1973, pp. 167-171, 2 pages.
Abstract of Article—Shaul M. Aharoni. "Hydrogen-Bonded Highly Regular Strictly Alternating Aliphatic-Aromatic Lquid Crystalline Poly(ester amides)," *Macromolecules*, Vo. 21, 1988, pp. 1941-1961.
Article—Li et al., "Modification of rheological properties of a thermotropic liquid crystalline polymer by melt-state reactive processing," *Polymer*, 2012, pp. 1-8.
Article—Shaul M. Aharoni, "Monodisperse Rodlike Oligomers and Their Mesomorphic Higher Molecular Weight Homologues," *Macromolecules*, vol. 20, No. 8, 1987, pp. 2010-2017.
Article—Siegmann et al., "Polyblends containing a liquid crystalline polymer," *Polymer*, 1985, vol. 26, August (conference issue), pp. 1325-1330.
Article—Dutta et al., "Polymer Blends Containing Liquid Crystals: A Review," *Polymer Engineering and Science*, Mid-Sep. 1990, vol. 30, No. 17, pp. 1005-1018.
Article—Oswal et al., "Synthesis and Characterization of Linear Aromatic Polyester-amides from Diacid Chlorides and Aminophenols," *Iranian Polymer Journal*, vol. 13, No. 3, 2004, pp. 205-212.
Abstract of Article—Preston et al., "Synthesis of high-molecular-weight rodlike polyamides and block copolymers," *Journal of Polymer Science: Polymer Chemistry Edition*, vol. 20, Issue 11, Nov. 1982, pp. 3241-3249.
Abstract of Article—Kajiyama et al., "Synthesis and properties of multiblock copolymers based on polydimethylsiloxane and piperazine-aromatic polyamides," *Journal of Applied Polymer Science*, vol. 39, Issue 8, Apr. 1990, pp. 1699-1708.
Abstract of Article—Ueda et al., "Synthesis of Sequential Polyamide by Direct Polycondensation," *Polymer Journal*, vol. 23, No. 3, 1991, pp. 167-176.
Article—Quamara et al., "Thermally stimulated depolarization current Investigations of copolyesteramide (Vectra B 950) polymer liquid crystal," *Materials Science-Poland*, vol. 28, No. 3, 2010, pp. 679-691.
Paper—Olena Rudko, "Liquid crystalline polymers. Uniaxial-biaxial nematic phase transition," *Term Paper for Physics 498, Emergent States of Matter*, May 6, 2002, pp. 112 (Department of Physics, University of Illinois at Urbana-Champaign).
Abstract of Article and Article—Ishida et al., "Unusual Thermal Behavior of the Aromatic Polyamide Dendrons," *Kobunshi Ronbunshu*, vol. 57, No. 12, Dec. 2000, pp. 825-829.
Search Report and Written Opinion for PCT/US2012/052436 dated Oct. 11, 2012, 13 pages.

\* cited by examiner

AROMATIC AMIDE COMPOUND

CROSS REFERENCE TO RELATED APPLICATIONS

The present application is a continuation of U.S. application Ser. No. 13/594,916, filed on Aug. 27, 2012, which claims priority to U.S. provisional application Ser. Nos. 61/528,445, filed on Aug. 29, 2011, and 61/664,911, filed on Jun. 27, 2012, which are incorporated herein in their entirety by reference thereto.

BACKGROUND OF THE INVENTION

High performance polymers, such as thermotropic liquid crystalline polymers ("LCPs"), are often used to form molded parts (e.g., electrical connectors). One benefit of such polymers is that they can exhibit a relatively high "flow", which refers to the ability of the polymer when heated under shear to uniformly fill complex parts at fast rates without excessive flashing or other detrimental processing issues. In addition to enabling complex part geometries, high polymer flow can also enhance the ultimate performance of the molded part. Most notably, parts generated from well-flowing polymers generally display improved dimensional stability owing to the lower molded-in stress, which makes the component more amenable to downstream thermal processes that can be negatively impacted from warpage and other polymer stress relaxation processes that occur in less well-molded materials. Despite their relatively high flow capacity, many high performance polymers still fall short of what is needed to meet the increased molding demands of intricate part designs without significant compromises to the final product performance. As such, a need continues to exist for a new compound that can be used in combination with high performance polymers, among other possible uses.

SUMMARY OF THE INVENTION

In accordance with one embodiment of the present invention, an aromatic amide compound is disclosed that has the following general formula (I):

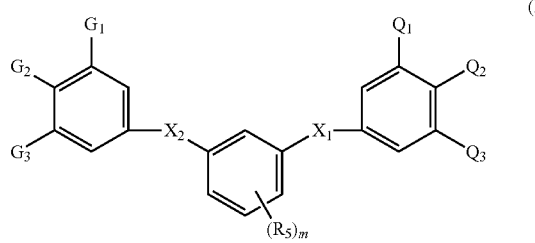

wherein,
$X_1$ and $X_2$ are independently C(O)HN or NHC(O);
$G_1$, $G_2$ and $G_3$ are independently hydrogen, C(O)HN-phenyl, or NHC(O)-phenyl, wherein at least one of $G_1$, $G_2$ and $G_3$ is C(O)HN-phenyl or NHC(O)-phenyl;
$Q_1$, $Q_2$, and $Q_3$ are independently hydrogen, C(O)HN-phenyl, or NHC(O)-phenyl, wherein at least one of $Q_1$, $Q_2$, and $Q_3$ is C(O)HN-phenyl or NHC(O)-phenyl;
$R_5$ is halo, haloalkyl, alkyl, alkenyl, aryl, heteroaryl, cycloalkyl, or heterocyclyl; and
m is from 0 to 4.

In accordance with another embodiment of the present invention, a method for forming an aromatic amide compound, such as represented above in formula (I), is disclosed. The method comprises reacting an aromatic acyl chloride with an amine-substituted phenyl to form an aminophenyl amide precursor, and thereafter, reacting the precursor with an aromatic diacyl chloride, aromatic triacyl chloride, or a combination thereof.

Other features and aspects of the present invention are set forth in greater detail below.

BRIEF DESCRIPTION OF THE FIGURES

A full and enabling disclosure of the present invention, including the best mode thereof to one skilled in the art, is set forth more particularly in the remainder of the specification, including reference to the accompanying figures, in which.

DETAILED DESCRIPTION OF REPRESENTATIVE EMBODIMENTS

Definitions

Figure 1:
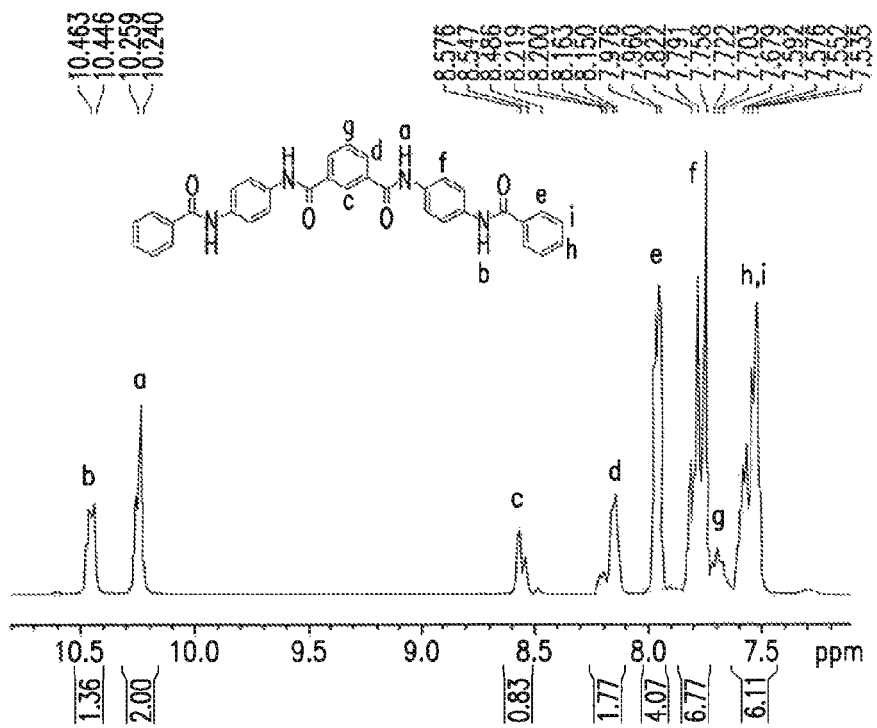
FIG. 1 is the Proton NMR characterization for N1,N3-bis (4-benzamidophenyl)benzene-1,3-dicarboxamide (Compound A2)

It is to be understood that the terminology used herein is for the purpose of describing particular embodiments only and is not intended to limit the scope of the present invention.

"Alkyl" refers to monovalent saturated aliphatic hydrocarbyl groups having from 1 to 10 carbon atoms and, in some embodiments, from 1 to 6 carbon atoms. "$C_{x-y}$alkyl" refers to alkyl groups having from x to y carbon atoms. This term includes, by way of example, linear and branched hydrocarbyl groups such as methyl ($CH_3$), ethyl ($CH_3CH_2$), n-propyl ($CH_3CH_2CH_2$), isopropyl (($CH_3)_2CH$), n-butyl ($CH_3CH_2CH2CH_2$), isobutyl (($CH_3)_2CHCH_2$), sec-butyl (($CH_3)(CH_3CH_2)CH$), t-butyl (($CH_3)_3C$), n-pentyl ($CH_3CH_2CH_2CH_2CH_2$), and neopentyl (($CH_3)_3CCH_2$).

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, ($C_x$-$C_y$)alkenyl refers to alkenyl groups having from x to y carbon atoms and is meant to include for example, ethenyl, propenyl, 1,3-butadienyl, and so forth.

"Alkynyl" refers to refers to a linear or branched monovalent hydrocarbon radical containing at least one triple bond. The term "alkynyl" may also include those hydrocarbyl groups having other types of bonds, such as a double bond and a triple bond.

"Aryl" refers to an aromatic group of from 3 to 14 carbon atoms and no ring heteroatoms and having a single ring (e.g., phenyl) or multiple condensed (fused) rings (e.g., naphthyl or anthryl). For multiple ring systems, including fused, bridged, and Spiro ring systems having aromatic and non-aromatic rings that have no ring heteroatoms, the term "Aryl" applies when the point of attachment is at an aromatic carbon atom (e.g., 5,6,7,8 tetrahydronaphthalene-2-yl is an aryl group as its point of attachment is at the 2-position of the aromatic phenyl ring).

"Cycloalkyl" refers to a saturated or partially saturated cyclic group of from 3 to 14 carbon atoms and no ring heteroatoms and having a single ring or multiple rings including fused, bridged, and Spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "cycloalkyl" includes cycloalkenyl groups, such as adamantyl, cyclopropyl, cyclobutyl, cyclopentyl, cyclooctyl, and cyclohexenyl. The term "cycloalkenyl" is sometimes employed to refer to a partially saturated cycloalkyl ring having at least one site of >C═C< ring unsaturation.

"Halo" or "halogen" refers to fluoro, chloro, bromo, and iodo.

"Haloalkyl" refers to substitution of alkyl groups with 1 to 5 or in some embodiments 1 to 3 halo groups.

"Heteroaryl" refers to an aromatic group of from 1 to 14 carbon atoms and 1 to 6 heteroatoms selected from oxygen, nitrogen, and sulfur and includes single ring (e.g. imidazolyl) and multiple ring systems (e.g. benzimidazol-2-yl and benzimidazol-6-yl). For multiple ring systems, including fused, bridged, and Spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N oxide (N→O), sulfinyl, or sulfonyl moieties. Examples of heteroaryl groups include, but are not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, or oxygen and includes single ring and multiple ring systems including fused, bridged, and Spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. decahydroquinolin-6-yl). In some embodiments, the nitrogen and/or sulfur atom(s) of the heterocyclic group are optionally oxidized to provide for the N oxide, sulfinyl, sulfonyl moieties. Examples of heterocyclyl groups include, but are not limited to, azetidinyl, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, thiomorpholinyl, imidazolidinyl, and pyrrolidinyl.

It should be understood that the aforementioned definitions encompass unsubstituted groups, as well as groups substituted with one or more other functional groups as is known in the art. For example, an aryl, heteroaryl, cycloalkyl, or heterocyclyl group may be substituted with from 1 to 8, in some embodiments from 1 to 5, in some embodiments from 1 to 3, and in some embodiments, from 1 to 2 substituents selected from alkyl, alkenyl, alkynyl, alkoxy, acyl, acylamino, acyloxy, amino, quaternary amino, amide, imino, amidino, aminocarbonylamino, amidinocarbonylamino, aminothiocarbonyl, aminocarbonylamino, aminothiocarbonylamino, aminocarbonyloxy, aminosulfonyl, aminosulfonyloxy, aminosulfonylamino, aryl, aryloxy, arylthio, azido, carboxyl, carboxyl ester, (carboxyl ester)amino, (carboxyl ester)oxy, cyano, cycloalkyl, cycloalkyloxy, cycloalkylthio, guanidino, halo, haloalkyl, haloalkoxy, hydroxy, hydroxyamino, alkoxyamino, hydrazino, heteroaryl, heteroaryloxy, heteroarylthio, heterocyclyl, heterocyclyloxy, heterocyclylthio, nitro, oxo, thione, phosphate, phosphonate, phosphinate, phosphonamidate, phosphorodiamidate, phosphoramidate monoester, cyclic phosphoramidate, cyclic phosphorodiamidate, phosphoramidate diester, sulfate, sulfonate, sulfonyl, substituted sulfonyl, sulfonyloxy, thioacyl, thiocyanate, thiol, alkylthio, etc., as well as combinations of such substituents.

"Compound" as used herein refers to a compound encompassed by the generic formulae disclosed herein, any subgenus of those generic formulae, and any forms of the compounds within the generic and subgeneric formulae, including the racemates, stereoisomers, tautomers, and salts of the compound.

"Stereoisomer" or "stereoisomers" refer to compounds that differ in the chirality of one or more stereocenters. Stereoisomers include enantiomers and diastereomers.

"Racemates" refers to a mixture of enantiomers.

"Tautomer" refer to alternate forms of a compound that differ in the position of a proton, such as enol keto and imine enamine tautomers, or the tautomeric forms of heteroaryl groups containing a ring atom attached to both a ring NH moiety and a ring ═N moiety such as pyrazoles, imidazoles, benzimidazoles, triazoles, and tetrazoles.

"Liquid crystalline polymer" or "liquid crystal polymer" refers to a polymer that can possess a rod-like structure that allows it to exhibit liquid crystalline behavior in its molten state (e.g., thermotropic nematic state). The polymer may contain aromatic units (e.g., aromatic polyesters, aromatic polyesteramides, etc.) so that it is wholly aromatic (e.g., containing only aromatic units) or partially aromatic (e.g., containing aromatic units and other units, such as cycloaliphatic units). The polymer may also be fully crystalline or semi-crystalline in nature.

DETAILED DESCRIPTION

It is to be understood by one of ordinary skill in the art that the present discussion is a description of exemplary embodiments only, and is not intended as limiting the broader aspects of the present invention.

The present invention is generally directed to an aromatic amide compound having the following general formula (I):

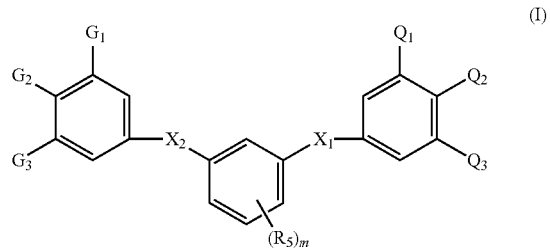

wherein, $X_1$ and $X_2$ are independently C(O)HN or NHC(O);

$G_1$, $G_2$ and $G_3$ are independently hydrogen, C(O)HN-phenyl, or NHC(O)-phenyl, wherein at least one of $G_1$, $G_2$ and $G_3$ is C(O)HN-phenyl or NHC(O)-phenyl;

$Q_1$, $Q_2$, and $Q_3$ are independently hydrogen, C(O)HN-phenyl, or NHC(O)-phenyl, wherein at least one of $Q_1$, $Q_2$, and $Q_3$ is C(O)HN-phenyl or NHC(O)-phenyl;

$R_5$ is halo, haloalkyl, alkyl, alkenyl, aryl, heteroaryl, cycloalkyl, or heterocyclyl; and m is from 0 to 4.

In certain embodiments, the compound is a di-functional compound in that the core phenyl ring is directly bonded to only two (2) amide groups (e.g., C(O)HN or NHC(O)). In such embodiments, m in Formula (I) may be 0. One particular embodiment of such a compound has the following general formula (II):

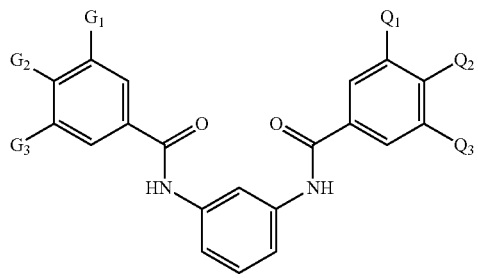

(II)

wherein, $G_1$, $G_2$, $Q_1$, and $Q_2$ are as defined above. For instance, $G_3$ and $Q_3$ are typically hydrogen. Further, in some embodiments, $G_1$ and $Q_1$ may be hydrogen and $G_2$ and $Q_2$ may be C(O)NH-phenyl or NHC(O)-phenyl. Alternatively, $G_2$ and $Q_2$ may be hydrogen and $G_1$ and $Q_1$ may be C(O)NH-phenyl or NHC(O)-phenyl.

Of course, the core phenyl ring may also be directly bonded to three (3) or more amide groups. For example, one particular embodiment of such a compound is provided by general (III):

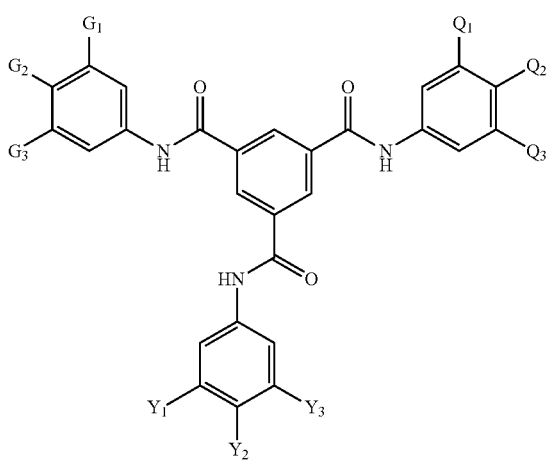

(III)

wherein, $G_1$, $G_2$, $G_3$, $Q_1$, $Q_2$, and $Q_3$ are as defined above; and $Y_1$, $Y_2$, and $Y_3$ are independently hydrogen, C(O)HN-phenyl, or NHC(O)-phenyl, wherein at least one of $Y_1$, $Y_2$, and $Y_3$ is C(O)HN-phenyl or NHC(O)-phenyl. For example, $Y_3$, $G_3$ and $Q_3$ are typically hydrogen. Further, in some embodiments, $Y_1$, $G_1$, and $Q_1$ may be hydrogen and $Y_2$, $G_2$ and $Q_2$ may be C(O)NH-phenyl or NHC(O)-phenyl. Alternatively, $Y_2$, $G_2$ and $Q_2$ may be hydrogen and $Y_1$, $G_1$ and $Q_1$ may be C(O)NH-phenyl or NHC(O)-phenyl.

Specific embodiments of the aromatic amide compound of the present invention are also set forth in the table below:

| Cmpd # | Structure | Name | MW (g/mol) |
|---|---|---|---|
| A1 | 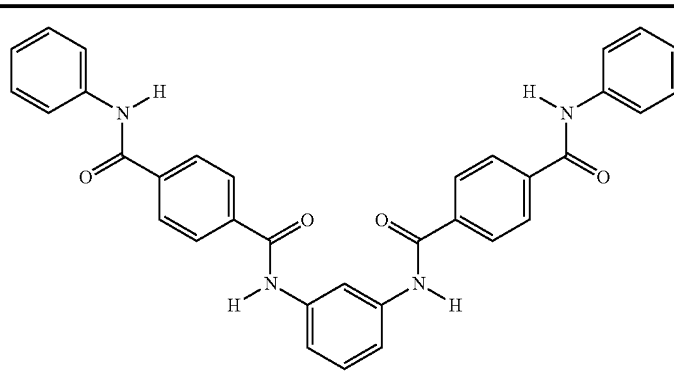 | N4-phenyl-N1-[3-[[4-(phenylcarbamoyl)-benzoyl]amino]phenyl]terephthalamide | 554.6 |

| Cmpd # | Structure | Name | MW (g/mol) |
|---|---|---|---|
| A2 | 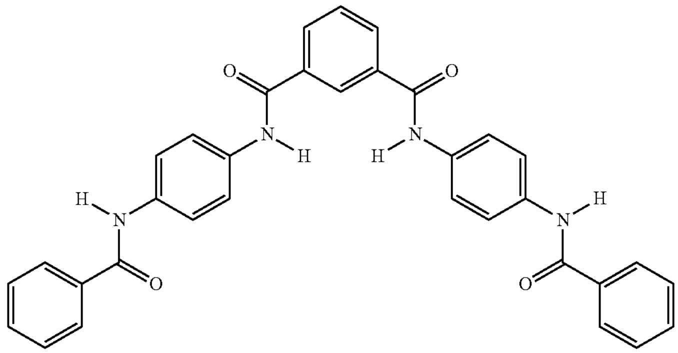 [SMILES: O=C(Nc1ccc(NC(=O)c2cccc(C(=O)Nc3ccc(NC(=O)c4ccccc4)cc3)c2)cc1)c1ccccc1] | N1,N3-bis(4-benzamidophenyl)benzene-1,3-dicarboxamide | 554.6 |
| B1 | 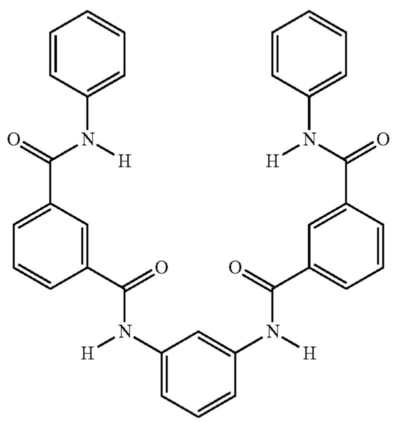 [SMILES: O=C(Nc1ccccc1)c1cccc(C(=O)Nc2cccc(NC(=O)c3cccc(C(=O)Nc4ccccc4)c3)c2)c1] | N3-phenyl-N1-[3-[[3-(phenylcarbamoyl)benzoyl]-amino]phenyl]benzene-1,3-dicarboxamide | 554.6 |
| B2 | 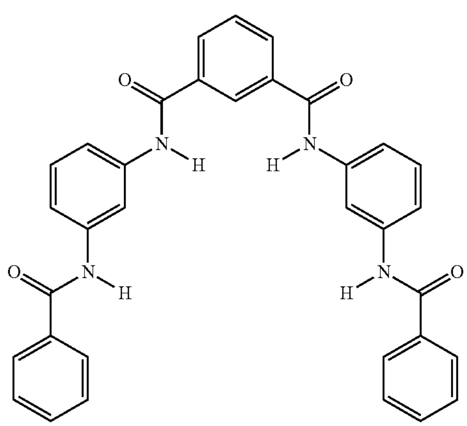 [SMILES: O=C(Nc1cccc(NC(=O)c2cccc(C(=O)Nc3cccc(NC(=O)c4ccccc4)c3)c2)c1)c1ccccc1] | N1,N3-bis(3-benzamidophenyl)benzene-1,3-dicarboxamide | 554.6 |

-continued

| Cmpd # | Structure | Name | MW (g/mol) |
|---|---|---|---|
| C | 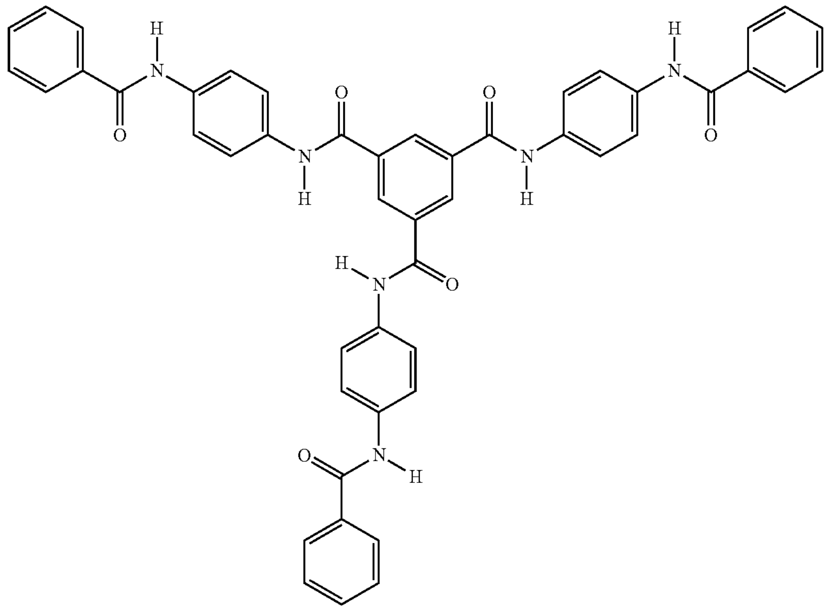 [SMILES: O=C(Nc1ccc(NC(=O)c2cc(C(=O)Nc3ccc(NC(=O)c4ccccc4)cc3)cc(C(=O)Nc3ccc(NC(=O)c4ccccc4)cc3)c2)cc1)c1ccccc1] | N1,N3,N5-tris(4-benzamidophenyl)benzene-1,3,5-tricarboxamide | 792.8 |
| D | 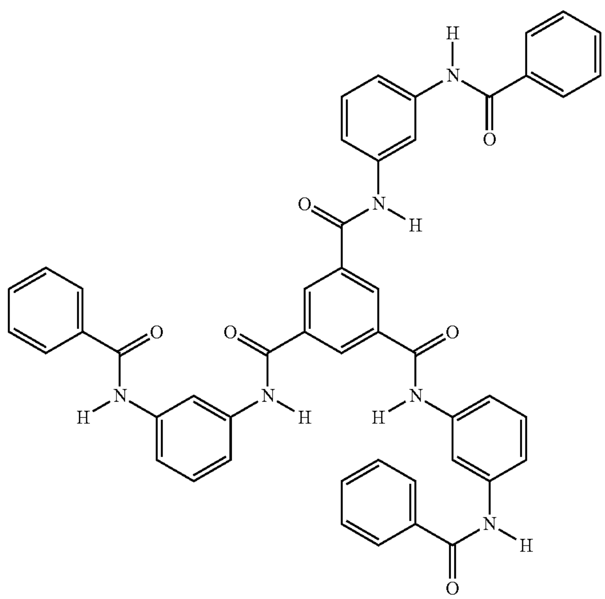 [SMILES: O=C(Nc1cccc(NC(=O)c2cc(C(=O)Nc3cccc(NC(=O)c4ccccc4)c3)cc(C(=O)Nc3cccc(NC(=O)c4ccccc4)c3)c2)c1)c1ccccc1] | N1,N3,N5-tris(3-benzamidophenyl)benzene-1,3,5-tricarboxamide | 792.8 |

The compounds disclosed herein may be prepared using a variety of different techniques. For example, a precursor aminophenyl amide may initially be formed by a nucleophilic addition/elimination reaction between an aromatic acyl chloride (e.g., benzoyl chloride) and a phenyl substituted with one or more amines (e.g., amine, diamine, triamine, etc.). Particular examples of such amine-substituted phenyls include 1,3-phenyldiamine and 1,4-phenyldiamine. The location of amine substitution on the phenyl ring can influence the resulting stereochemistry of the amide precursor. For example, the reaction of a benzoyl chloride with 1,3-phenyldiamine may result in a 3-aminophenyl substituted benzamide precursor having the following structure:

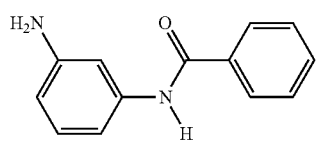 [SMILES: Nc1cccc(NC(=O)c2ccccc2)c1]

Likewise, a reaction with 1,4-phenyldiamine may result in a 4-aminophenyl substituted benzamide precursor having the following structure:

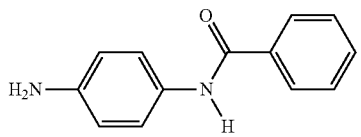 [SMILES: Nc1ccc(NC(=O)c2ccccc2)cc1]

Regardless, the resulting amide precursor may be further reacted with a diacyl and/or triacyl chloride to achieve the desired compound. Diacyl chlorides (e.g., isophthaloyl chloride), for instance, typically result in "ditopic" compounds in which the core phenyl ring is bonded to only two amide groups, while triacyl chlorides (e.g., trimesoyl chloride) typically result in "tritopic" compounds in which the core phenyl ring is bonded to three amide groups. Such techniques for forming the compound of the present invention are described in more detail in the examples below. It will be appreciated that where process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Additionally, as will be apparent to those skilled in the art, compounds that contain one or more chiral centers can be prepared or isolated as pure stereoisomers, i.e., as individual enantiomers or diastereomers, or as stereoisomer-enriched mixtures. All such stereoisomers (and enriched mixtures) are included within the scope of this invention. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and so forth.

The compound of the present invention may have a variety of different uses. For instance, the present inventors have discovered that they can act as flow aids for thermotropic liquid crystalline polymers by altering intermolecular polymer chain interactions, thereby lowering the overall viscosity of the polymer matrix under shear. In addition to simply reducing viscosity, the aromatic amide compound may not be easily volatized or decomposed during compounding, molding, and/or use. This minimizes off-gassing and the formation of blisters that would otherwise impact the final mechanical properties of a part made from the polymer composition. Without intending to be limited by theory, it is believed that active hydrogen atoms of the amide functional groups are capable of forming a hydrogen bond with the backbone of liquid crystalline polyesters or polyesteramides. Such hydrogen bonding strengthens the attachment of the compound to the liquid crystalline polymer matrix and thus minimizes the likelihood that it becomes volatilized during formation. While providing the benefits noted, the aromatic amide compound does not generally react with the polymer backbone of the liquid crystalline polymer to any appreciable extent so that the mechanical properties of the polymer are not adversely impacted.

When employed as a flow aid, the aromatic amide compound of the present invention typically has a relatively low molecular weight. For example, the compound may have a molecular weight of about 2,500 grams per mole or less, in some embodiments from about 200 to about 1,500 grams per mole, in some embodiments from about 300 to about 1,200 grams per mole, and in some embodiments, from about 400 to about 1,000 grams per mole. The compound may also generally possess a high amide functionality so it is capable of undergoing a sufficient degree of hydrogen bonding with the liquid crystalline polymer. The degree of amide functionality for a given molecule may be characterized by its "amide equivalent weight", which reflects the amount of a compound that contains one molecule of an amide functional group and may be calculated by dividing the molecular weight of the compound by the number of amide groups in the molecule. For example, the aromatic amide compound may contain from 4 to 8, and in some embodiments, from 4 to 6 amide functional groups per molecule. The amide equivalent weight may likewise be from about 10 to about 1,000 grams per mole or less, in some embodiments from about 50 to about 500 grams per mole, and in some embodiments, from about 100 to about 300 grams per mole.

The type of thermotropic liquid crystalline polymers that may be employed in combination with the compound of the present invention can vary as is known in the art. Suitable liquid crystalline polymers are generally condensation polymers that have relatively rigid and linear polymer chains so that they melt to form a liquid crystalline phase. Examples of such polymers may include, for instance, aromatic or aliphatic polyesters, aromatic or aliphatic poly(esteramides), aromatic or aliphatic poly(estercarbonates), aromatic or aliphatic polyamides, etc. Such polymers may, for example, contain repeating units formed from one or more aromatic or aliphatic hydroxycarboxylic acids, aromatic or aliphatic dicarboxylic acids, aromatic or aliphatic diols, aromatic or aliphatic aminocarboxylic acids, aromatic or aliphatic amines, aromatic or aliphatic diamines, etc., as well as combinations thereof.

Particularly suitable aromatic polyesters are obtained by polymerizing (1) two or more aromatic hydroxycarboxylic acids; (2) at least one aromatic hydroxycarboxylic acid, at least one aromatic dicarboxylic acid, and at least one aromatic diol; and/or (3) at least one aromatic dicarboxylic acid and at least one aromatic diol. Examples of suitable aromatic hydroxycarboxylic acids include, 4-hydroxybenzoic acid; 4-hydroxy-4'-biphenylcarboxylic acid; 2-hydroxy-6-naphthoic acid; 2-hydroxy-5-naphthoic acid; 3-hydroxy-2-naphthoic acid; 2-hydroxy-3-naphthoic acid; 4'-hydroxyphenyl-4-benzoic acid; 3'-hydroxyphenyl-4-benzoic acid; 4'-hydroxyphenyl-3-benzoic acid, etc., as well as alkyl, alkoxy, aryl and halogen substituents thereof. Examples of suitable aromatic dicarboxylic acids include terephthalic acid; isophthalic acid; 2,6-naphthalenedicarboxylic acid; diphenyl ether-4,4'-dicarboxylic acid; 1,6-naphthalenedicarboxylic acid; 2,7-naphthalenedicarboxylic acid; 4,4'-dicarboxybiphenyl; bis(4-carboxyphenyl)ether; bis(4-carboxyphenyl)butane, bis(4-carboxyphenyl)ethane; bis(3-carboxyphenyl)ether, bis(3-carboxyphenyl)ethane, etc., as well as alkyl, alkoxy, aryl and halogen substituents thereof. Examples of suitable aromatic diols include hydroquinone; resorcinol; 2,6-dihydroxynaphthalene; 2,7-dihydroxynaphthalene; 1,6-dihydroxynaphthalene; 4,4'-dihydroxybiphenyl; 3,3'-dihydroxybiphenyl; 3,4'-dihydroxybiphenyl; 4,4'-dihydroxybiphenyl ether; bis(4-hydroxyphenyl)ethane, etc., as well as alkyl, alkoxy, aryl and halogen substituents thereof. In one particular embodiment, the aromatic polyester contains monomer repeat units derived from 4-hydroxybenzoic acid and 2,6-hydroxynaphthoic acid. The monomer units derived from 4-hydroxybenzoic acid may constitute from about 45% to about 85% (e.g., 73%) of the polymer on a mole basis and the monomer units derived from 2,6-hydroxynaphthoic acid may constitute from about 15% to about 55% (e.g., 27%) of the polymer on a mole basis. Such aromatic polyesters are commercially available from Ticona, LLC under the trade designation VECTRA® A. The synthesis and structure of these and other aromatic polyesters may be described in more detail in U.S. Pat. Nos. 4,161,470; 4,473,682; 4,522,974; 4,375,530; 4,318,841; 4,256,624; 4,219,461; 4,083,829; 4,184,996; 4,279,803; 4,337,190; 4,355,134; 4,429,105; 4,393,191; 4,421,908; 4,434,262; and 5,541,240.

Liquid crystalline polyesteramides may also include those obtained by polymerizing (1) at least one aromatic hydroxycarboxylic acid and at least one aromatic aminocarboxylic acid; (2) at least one aromatic hydroxycarboxylic acid, at least one aromatic dicarboxylic acid, and at least one aromatic amine and/or diamine optionally having phenolic hydroxy groups; and (3) at least one aromatic dicarboxylic acid and at least one aromatic amine and/or diamine optionally having phenolic hydroxy groups. Suitable aromatic amines and diamines may include, for instance, 3-aminophenol; 4-aminophenol; 1,4-phenylenediamine; 1,3-phenylenediamine, etc., as well as alkyl, alkoxy, aryl and halogen substituents thereof. In one particular embodiment, the aromatic polyesteramide contains monomer units derived from 2,6-hydroxynaphthoic acid, terephthalic acid, and 4-aminophenol. The monomer units derived from 2,6-hydroxynaphthoic acid may constitute from about 35% to about 85% of the polymer on a mole basis (e.g., 60%), the monomer units derived from terephthalic acid may constitute from about 5% to about 50% (e.g., 20%) of the polymer on a mole basis, and the monomer units derived from 4-aminophenol may constitute from about 5% to about 50% (e.g., 20%) of the polymer on a mole basis. Such aromatic polyesters are commercially available from Ticona, LLC under the trade designation VECTRA® B. In another embodiment, the aromatic polyesteramide contains monomer units derived from 2,6-hydroxynaphthoic acid, and 4-hydroxybenzoic acid, and 4-aminophenol, as well as other optional monomers (e.g., 4,4'-dihydroxybiphenyl and/or terephthalic acid). The synthesis and structure of these and other aromatic poly(esteramides) may be described in more detail in U.S. Pat. Nos. 4,339,375; 4,355,132; 4,351,917; 4,330,457; 4,351,918; and 5,204,443.

The liquid crystalline polymer typically has a number average molecular weight (Mn) of about 2,000 grams per mole or more, in some embodiments from about 4,000 grams per mole or more, and in some embodiments, from about 5,000 to about 30,000 grams per mole. Of course, it is also possible to form polymers having a lower molecular weight, such as less than about 2,000 grams per mole. The intrinsic viscosity of the polymer composition, which is generally proportional to molecular weight, may likewise be about 2 deciliters per gram ("dlg") or more, in some embodiments about 3 dL/g or more, in some embodiments from about 4 to about 20 dL/g, and in some embodiments from about 5 to about 15 dL/g. Intrinsic viscosity may be determined in accordance with ISO-1628-5 using a 50/50 (v/v) mixture of pentafluorophenol and hexafluoroisopropanol, as described in more detail below.

The relative proportion of the liquid crystalline polymer and the aromatic amide compound may be selected to help achieve a balance between viscosity and mechanical properties. More particularly, high aromatic amide compound contents can result in low viscosity, but too high of a content may reduce the viscosity to such an extent that the compound adversely impacts the melt strength of the polymer blend. In most embodiments, for example, the aromatic amide compound, or mixtures thereof, may be employed in an amount of from about 0.1 to about 5 parts, in some embodiments from about 0.2 to about 4 parts, and in some embodiments, from about 0.3 to about 1.5 parts by weight relative to 100 parts by weight of the liquid crystalline polymer. Aromatic amide compounds may, for example, constitute from about 0.1 wt. % to about 5 wt. %, in some embodiments from about 0.2 wt. % to about 4 wt. %, and in some embodiments, from about 0.3 wt. % to about 1.5 wt. % of the polymer composition. Liquid crystalline polymers may likewise constitute from about 95 wt. % to about 99.9 wt. %, in some embodiments from about 96 wt. % to about 98.8 wt. %, and in some embodiments, from about 98.5 wt. % to about 99.7 wt. % of the polymer composition.

The manner in which the compound and the liquid crystalline polymer are combined may vary as is known in the art. For instance, the raw materials may be supplied either simultaneously or in sequence to a melt processing device that dispersively blends the materials. Batch and/or continuous melt processing techniques may be employed. For example, a mixer/kneader, Banbury mixer, Farrel continuous mixer, single-screw extruder, twin-screw extruder, roll mill, etc., may be utilized to blend and melt process the materials. One particularly suitable melt processing device is a co-rotating, twin-screw extruder (e.g., Leistritz co-rotating fully intermeshing twin screw extruder). Such extruders may include feeding and venting ports and provide high intensity distributive and dispersive mixing. For example, the liquid crystalline polymer and compound may be fed to the same or different feeding ports of a twin-screw extruder and melt blended to form a substantially homogeneous melted mixture. Melt blending may occur under high shear/pressure and heat to ensure sufficient dispersion. For example, melt processing may occur at a temperature of from about 50° C. to about 500° C., and in some embodiments, from about 100° C. to about 250° C. Likewise, the apparent shear rate during melt processing may range from about 100 seconds-1 to about 10,000 seconds-1, and in some embodiments, from about 500 seconds-1 to about 1,500 seconds-1. Of course, other variables, such as the residence time during melt processing, which is inversely proportional to throughput rate, may also be controlled to achieve the desired degree of homogeneity.

Besides melt blending, other techniques may also be employed to combine the compound and the liquid crystalline polymer. For example, the compound may be supplied during one or more stages of the polymerization of the liquid crystalline polymer. In such embodiments, it is typically desired to apply the compound before melt polymerization has been initiated, and typically in conjunction with the precursor monomers for the liquid crystalline polymer. Regardless of the manner in which it is introduced, the aromatic amide compound may lower the melt viscosity of the resulting polymer composition. The melt viscosity may, for instance, be reduced so that the ratio of the starting liquid crystalline polymer viscosity to the blended composition viscosity is at least about 1.1, in some embodiments at least about 1.2, in some embodiments from about 1.5 to about 50, in some embodiments from about 2 to about 40, and in some embodiments, from about 4 to about 30. In one particular embodiment, the polymer composition may have a melt viscosity of from about 0.5 to about 100 Pa-s, in some embodiments from about 1 to about 80 Pa-s, and in some embodiments, from about 2 to about 50 Pa-s, determined at a shear rate of 1000 seconds-1. Melt viscosity may be determined in accordance with ISO Test No. 11443 (equivalent to ASTM Test No. 1238-70) at a temperature of 350° C. The melting point of the polymer composition may also range from about 250° C. to about 400° C., in some embodiments from about 270° C. to about 380° C., and in some embodiments, from about 300° C.

to about 360° C. Likewise, the crystallization temperature may range from about 200° C. to about 400° C., in some embodiments from about 250° C. to about 350° C., and in some embodiments, from about 280° C. to about 320° C. The melting and crystallization temperatures may be determined as is well known in the art using differential scanning calorimetry ("DSC"), such as determined by ISO Test No. 11357.

If desired, the resulting polymer composition may also be combined with a wide variety of other types of components to form a filled composition. For example, a filler material may be incorporated with the polymer composition to enhance strength. A filled composition can include a filler material such as a fibrous filler and/or a mineral filler and optionally one or more additional additives as are generally known in the art.

Mineral fillers may, for instance, be employed in the polymer composition to help achieve the desired mechanical properties and/or appearance. When employed, mineral fillers typically constitute from about 5 wt. % to about 60 wt. %, in some embodiments from about 10 wt. % to about 55 wt. %, and in some embodiments, from about 20 wt. % to about 50 wt. % of the polymer composition. Clay minerals may be particularly suitable for use in the present invention. Examples of such clay minerals include, for instance, talc ($Mg_3Si_4O_{10}(OH)_2$), halloysite ($Al_2Si_2O_5(OH)_4$), kaolinite ($Al_2Si_2O_5(OH)_4$), illite (($K,H_3O)(Al,Mg,Fe)_2(Si,Al)_4O_{10}[(OH)_2,(H_2O)]$), montmorillonite ($(Na,Ca)_{0.33}(Al,Mg)_2Si_4O_{10}(OH)_2 \cdot nH_2O$), vermiculite (($MgFe,Al)_3(Al,Si)_4O_{10}(OH)_2 \cdot 4H_2O$), palygorskite (($Mg,Al)_2Si_4O_{10}(OH) \cdot 4(H_2O)$), pyrophyllite ($Al_2Si_4O_{10}(OH)_2$), etc., as well as combinations thereof. In lieu of, or in addition to, clay minerals, still other mineral fillers may also be employed. For example, other suitable silicate fillers may also be employed, such as calcium silicate, aluminum silicate, mica, diatomaceous earth, wollastonite, and so forth. Mica, for instance, may be particularly suitable. There are several chemically distinct mica species with considerable variance in geologic occurrence, but all have essentially the same crystal structure. As used herein, the term "mica" is meant to generically include any of these species, such as muscovite ($KAl_2(AlSi_3)O_{10}(OH)_2$), biotite ($K(Mg,Fe)_3(AlSi_3)O_{10}(OH)_2$), phlogopite ($KMg_3(AlSi_3)O_{10}(OH)_2$), lepidolite ($K(Li,Al)_{2-3}(AlSi_3)O_{10}(OH)_2$), glauconite ($(K,Na)(Al,Mg,Fe)_2(Si,Al)_4O_{10}(OH)_2$), etc., as well as combinations thereof.

Fibers may also be employed as a filler material to further improve the mechanical properties. Such fibers generally have a high degree of tensile strength relative to their mass. For example, the ultimate tensile strength of the fibers (determined in accordance with ASTM D2101) is typically from about 1,000 to about 15,000 Megapascals ("MPa"), in some embodiments from about 2,000 MPa to about 10,000 MPa, and in some embodiments, from about 3,000 MPa to about 6,000 MPa. To help maintain an insulative property, which is often desirable for use in electronic components, the high strength fibers may be formed from materials that are also generally insulative in nature, such as glass, ceramics (e.g., alumina or silica), aramids (e.g., Kevlar® marketed by E. I. duPont de Nemours, Wilmington, Del.), polyolefins, polyesters, etc., as well as mixtures thereof. Glass fibers are particularly suitable, such as E-glass, A-glass, C-glass, D-glass, AR-glass, R-glass, S1-glass, S2-glass, etc., and mixtures thereof.

The volume average length of the fibers may be from about 50 to about 400 micrometers, in some embodiments from about 80 to about 250 micrometers, in some embodiments from about 100 to about 200 micrometers, and in some embodiments, from about 110 to about 180 micrometers. The fibers may also have a narrow length distribution. That is, at least about 70% by volume of the fibers, in some embodiments at least about 80% by volume of the fibers, and in some embodiments, at least about 90% by volume of the fibers have a length within the range of from about 50 to about 400 micrometers, in some embodiments from about 80 to about 250 micrometers, in some embodiments from about 100 to about 200 micrometers, and in some embodiments, from about 110 to about 180 micrometers. The fibers may also have a relatively high aspect ratio (average length divided by nominal diameter) to help improve the mechanical properties of the resulting polymer composition. For example, the fibers may have an aspect ratio of from about 2 to about 50, in some embodiments from about 4 to about 40, and in some embodiments, from about 5 to about 20 are particularly beneficial. The fibers may, for example, have a nominal diameter of about 10 to about 35 micrometers, and in some embodiments, from about 15 to about 30 micrometers.

The relative amount of the fibers in the filled polymer composition may also be selectively controlled to help achieve the desired mechanical properties without adversely impacting other properties of the composition, such as its flowability. For example, the fibers may constitute from about 2 wt. % to about 40 wt. %, in some embodiments from about 5 wt. % to about 35 wt. %, and in some embodiments, from about 6 wt. % to about 30 wt. % of the polymer composition. Although the fibers may be employed within the ranges noted above, small fiber contents may be employed while still achieving the desired mechanical properties. For example, the fibers can be employed in small amounts such as from about 2 wt. % to about 20 wt. %, in some embodiments, from about 5 wt. % to about 16 wt. %, and in some embodiments, from about 6 wt. % to about 12 wt. %.

Still other additives that can be included in the composition may include, for instance, antimicrobials, pigments (e.g., carbon black), antioxidants, stabilizers, surfactants, waxes, solid solvents, and other materials added to enhance properties and processability. Lubricants, for instance, may be employed in the polymer composition. Examples of such lubricants include fatty acids esters, the salts thereof, esters, fatty acid amides, organic phosphate esters, and hydrocarbon waxes of the type commonly used as lubricants in the processing of engineering plastic materials, including mixtures thereof. Suitable fatty acids typically have a backbone carbon chain of from about 12 to about 60 carbon atoms, such as myristic acid, palmitic acid, stearic acid, arachic acid, montanic acid, octadecinic acid, parinric acid, and so forth. Suitable esters include fatty acid esters, fatty alcohol esters, wax esters, glycerol esters, glycol esters and complex esters. Fatty acid amides include fatty primary amides, fatty secondary amides, methylene and ethylene bisamides and alkanolamides such as, for example, palmitic acid amide, stearic acid amide, oleic acid amide, N,N'-ethylenebisstearamide and so forth. Also suitable are the metal salts of fatty acids such as calcium stearate, zinc stearate, magnesium stearate, and so forth; hydrocarbon waxes, including paraffin waxes, polyolefin and oxidized polyolefin waxes, and microcrystalline waxes. Particularly suitable lubricants are acids, salts, or amides of stearic acid, such as pentaerythritol tetrastearate, calcium stearate, or N,N'-ethylenebisstearamide. When employed, the lubricant(s) typically constitute from about 0.05 wt. % to about 1.5 wt. %, and in some embodiments, from about 0.1 wt. % to about 0.5 wt. % (by weight) of the polymer composition.

The present invention may be better understood with reference to the following examples.

Test Methods

Melt Viscosity:

The melt viscosity (Pa-s) was determined in accordance with ISO Test No. 11443 at 350° C. and at a shear rate of 400 $s^{-1}$ and 1000 $s^{-1}$ using a Dynisco 7001 capillary rheometer. The rheometer orifice (die) had a diameter of 1 mm, length of 20 mm, L/D ratio of 20.1, and an entrance angle of 180°. The diameter of the barrel was 9.55 mm±0.005 mm and the length of the rod was 233.4 mm.

Intrinsic Viscosity:

The intrinsic viscosity ("IV") may be measured in accordance with ISO-1628-5 using a 50/50 (v/v) mixture of pentafluorophenol and hexafluoroisopropanol. Each sample was prepared in duplicate by weighing about 0.02 grams into a 22 mL vial, 10 mL of pentafluorophenol ("PFP") was added to each vial and the solvent. The vials were placed in a heating block set to 80° C. overnight. The following day 10 mL of hexafluoroisopropanol ("HFIP") was added to each vial. The final polymer concentration of each sample was about 0.1%. The samples were allowed to cool to room temperature and analyzed using a PolyVisc automatic viscometer.

Melting and Crystallization Temperatures:

The melting temperature ("Tm") and crystallization temperature ("Tc") were determined by differential scanning calorimetry ("DSC") as is known in the art. The melting temperature is the differential scanning calorimetry (DSC) peak melt temperature as determined by ISO Test No. 11357. The crystallization temperature is determined from the cooling exotherm in the cooling cycle. Under the DSC procedure, samples were heated and cooled at 20° C. per minute as stated in ISO Standard 10350 using DSC measurements conducted on a TA Q2000 Instrument.

Tensile Properties:

Tensile properties are tested according to ISO Test No. 527 (technically equivalent to ASTM D638). Modulus and strength measurements are made on the same test strip sample having a length of 80 mm, thickness of 10 mm, and width of 4 mm. The testing temperature is 23° C., and the testing speeds are 1 or 5 mm/min.

Flexural Properties:

Flexural properties are tested according to ISO Test No. 178 (technically equivalent to ASTM D790). This test is performed on a 64 mm support span. Tests are run on the center portions of uncut ISO 3167 multi-purpose bars. The testing temperature is 23° C. and the testing speed is 2 mm/min.

Notched Charpy Impact Strength:

Notched Charpy properties are tested according to ISO Test No. ISO 179-1) (technically equivalent to ASTM D256, Method B). This test is run using a Type A notch (0.25 mm base radius) and Type 1 specimen size (length of 80 mm, width of 10 mm, and thickness of 4 mm). Specimens are cut from the center of a multi-purpose bar using a single tooth milling machine. The testing temperature is 23° C.

Synthesis of N1,N3-bis(4-benzamidophenyl)-benzene-1,3-dicarboxamide Compound A2

The synthesis of Compound A2 from 1,4-phenylene diamine, terephthaloyl chloride, and benzoyl chloride may be performed according to the following scheme:

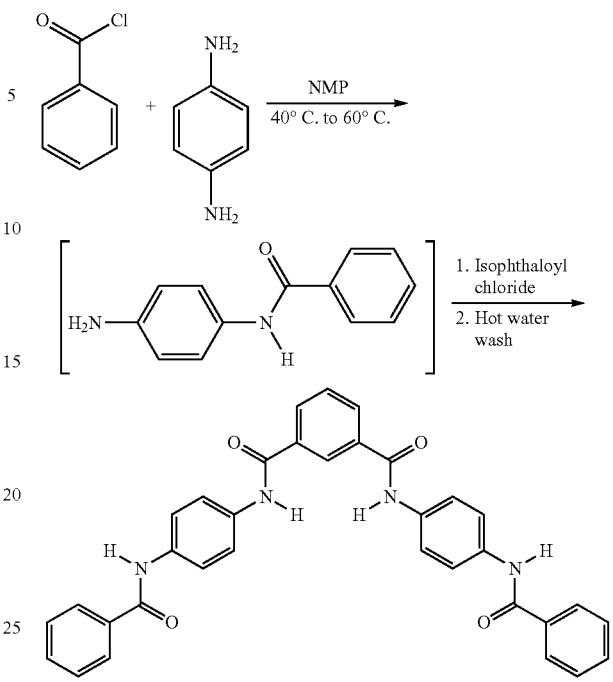

The experimental setup consisted of a 500 mL glass beaker equipped with a magnetic stirrer. 1,4 phenylene diamine (20 g) was dissolved in warm N-methyl pyrrolidone ("NMP") (200 mL) at 40° C. Benzoyl chloride (26.51 g) was added drop wise to a stirred solution of the diamine over a period of 30 minutes. After the addition of the benzoyl chloride was completed, the reaction mixture was warmed to 70-80° C. and then allowed to cool to 50° C. After cooling to the desired temperature, isophthaloyl chloride (18.39 g) was added in small portions such that the temperature of the reaction mixture did not increase above 70° C. The mixture was then stirred for additional one (1) hour at 70° C., and was allowed to rest overnight at room temperature. The product was recovered by addition of water (200 mL) to the reaction mixture, followed by filtration and washing with hot water (500 mL). The product was then dried in a vacuum oven at 150° C. for about 6-8 hours to give a pale yellow colored solid (yield ca. 90%). The melting point by DSC analysis was determined to be 329° C. The Proton NMR characterization for the compound is also shown in FIG. 1.

Synthesis of N1,N3-bis(3-benzamidophenyl)benzene-1,3-dicarboxamide Compound B2

The synthesis of Compound B2 from 1,3-phenylene diamine, isophthaloyl chloride, and benzoyl chloride may be performed according to the following scheme:

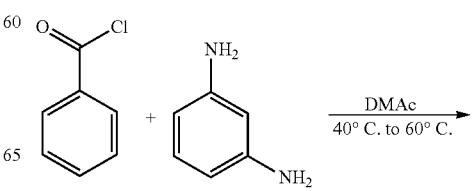

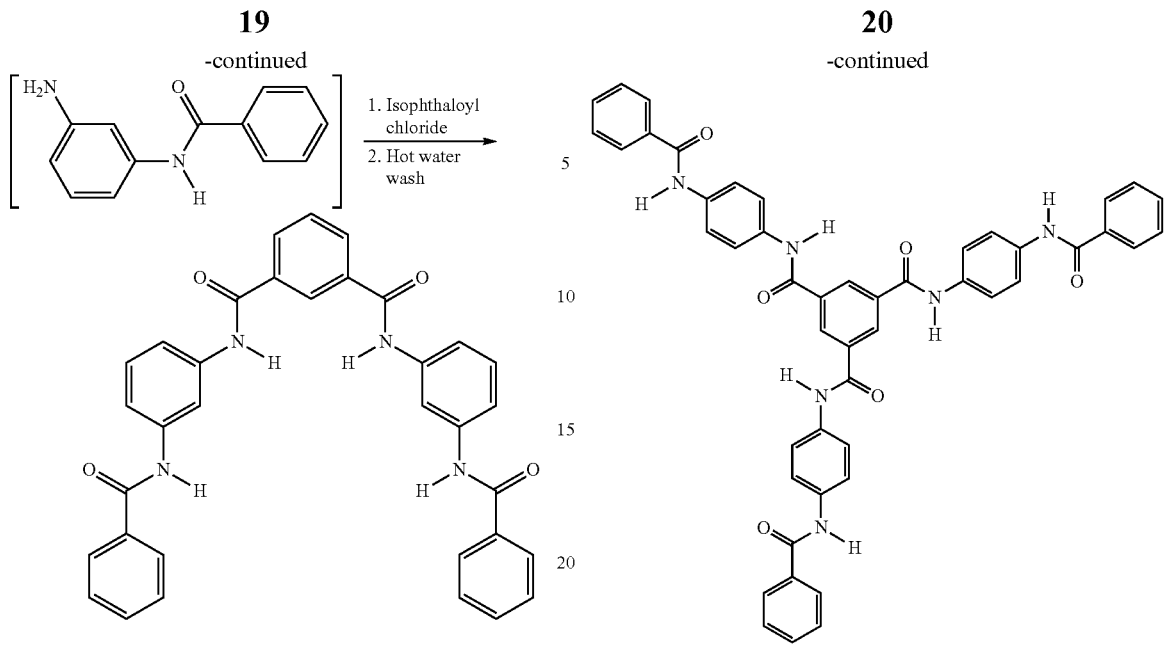

Figure 2:
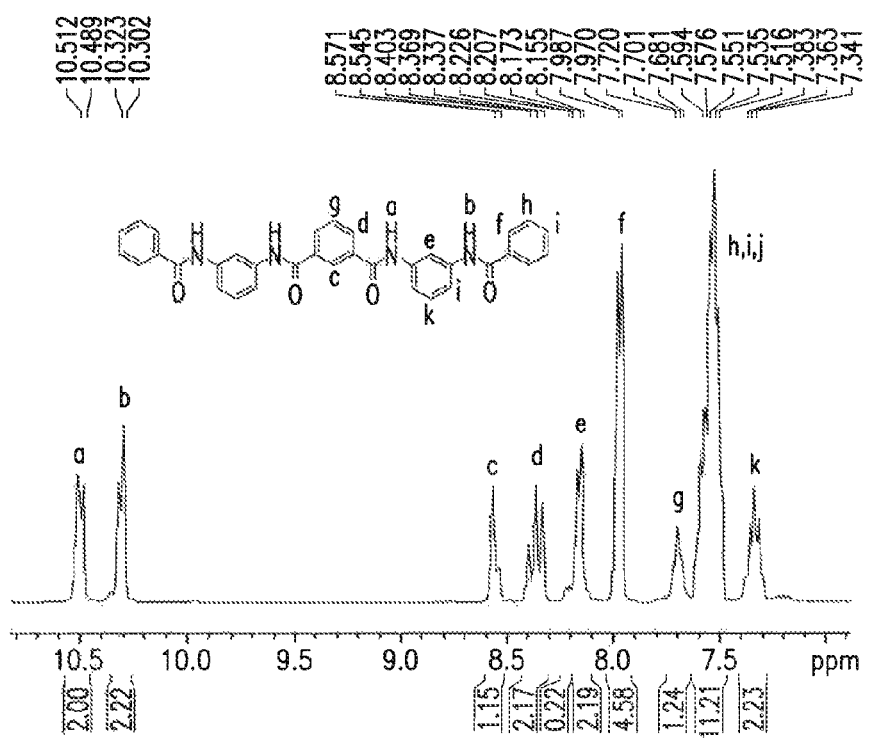
FIG. 2 is the Proton NMR characterization for N1,N3-bis (3-benzamidophenyl)benzene-1,3-dicarboxamide (Compound B2)

The experimental setup consisted of a 500 mL glass beaker equipped with a magnetic stirrer. 1,3 phenylene diamine (20 g) was dissolved in warm dimethylacetamide ("DMAc") (200 mL) at 40° C. Benzoyl chloride (26.51 g) was added drop wise to a stirred solution of the diamine over a period of 30 minutes. After the addition of the benzoyl chloride was completed, the reaction mixture was warmed to 70-80° C. and allowed to cool to 50° C. After cooling to the desired temperature, isophthaloyl chloride (18.39 g) was added in small portions such that the temperature of the reaction mixture did not increase above 70° C. The mixture was then stirred for additional one hour at 70° C., and was allowed to rest overnight at room temperature. The product was recovered by addition of water (200 mL) to the reaction mixture, followed by filtration and washing with hot water (500 mL). The product was then dried in a vacuum oven at 150° C. for about 6-8 hours to give a pale yellow colored solid (yield ca. 90%). The melting point by DSC analysis was determined to be 226° C. The Proton NMR characterization for the compound is shown in FIG. 2.

Synthesis of N1,N3,N5-tris(4-benzamidophenyl)benzene-1,3,4-tricarboxamide Compound C The synthesis of Compound C from trimesoyl chloride and 4-benzanilide may be performed according to the following scheme:

The experimental set up consisted of a 1 L glass beaker equipped with a glass rod stirrer coupled with an overhead mechanical stirrer. Trimesoyl chloride (27.08 g) was dissolved in DMAc (100 mL) at room temperature. 4-aminobenzanilide (69.3 g) was dissolved in DMAc (100 mL). The amine solution was gradually added to the acid chloride solution over a period of 15 minutes, and the reaction mixture was then stirred and the temperature increased to 90° C. for about 3 hours. The mixture was allowed to rest overnight at room temperature. The product was recovered by precipitation through the addition of 1.5 L of distilled water, which was followed by was vacuum filtration using a filter paper and a Buchner funnel. The crude product was then washed with acetone (500 mL) and washed again with hot water (1 L). The product was then air dried over night at room temperature and then was dried in a vacuum oven 150° C. for 4 to 6 hours. The product (68 g) was a bright yellow solid.

Compound C can also be synthesized by a different synthetic route i.e., from trimesoyl chloride and 1,4-phenylene diamine as follows:

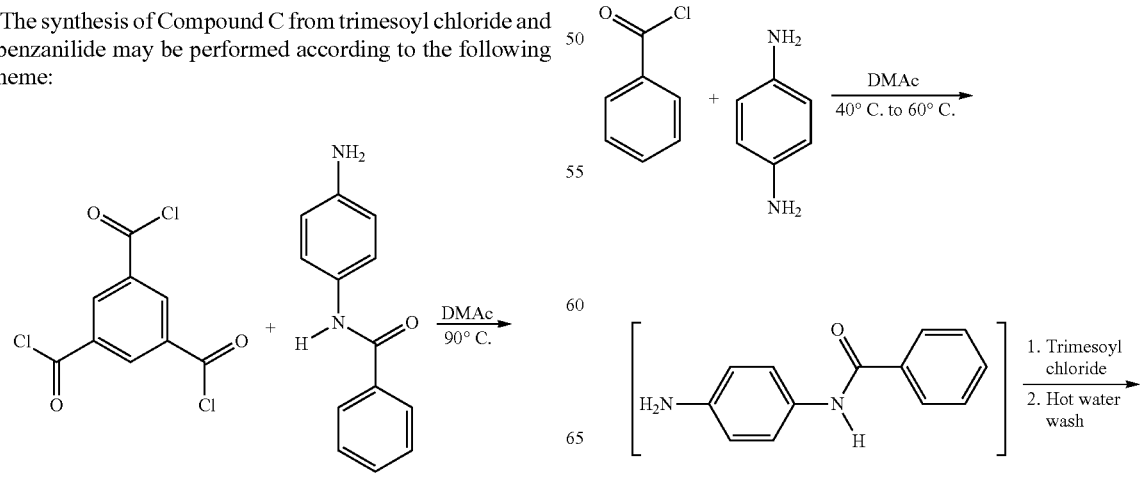

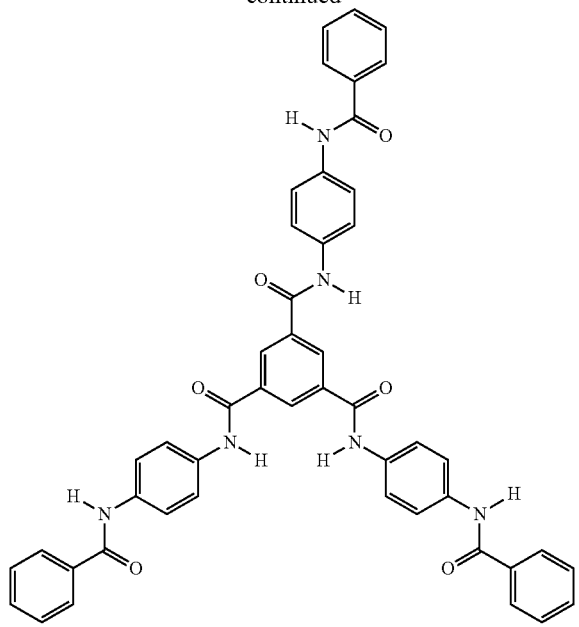

The experimental set up consisted of a 2 L glass beaker equipped with a glass rod stirrer coupled with an overhead mechanical stirrer. 1,4 phenylene diamine (250.41 g) was dissolved in warm dimethyl acetamide (1.5 L) (alternatively N-methyl pyrrolidone can also be used) and maintained at 45° C. Next benzoyl chloride (332.11 g) was slowly added drop wise over a period of 1.5 to 2 hours, to the amine solution with constant stirring. The rate of addition of the benzoyl chloride was maintained such that the reaction temperature was maintained less than 60° C. After complete addition of the benzoyl chloride, the reaction mixture was gradually warmed to 85-90° C. and then allowed to cool to around 45-50° C. At this point, trimesoyl chloride (200.7 g) was gradually added to the reaction mixture such that the exotherm did not increase the reaction temperature above 60° C. After complete addition of the trimesoyl chloride, the reaction mixture was allowed to stir for additional 45 minutes, after which the reaction temperature was increased to 90° C. for about 30 minutes and then was cooled to room temperature. The mixture was allowed to rest overnight at room temperature. The product was recovered by precipitation through the addition of 1.5 L of distilled water, which was followed by was vacuum filtration using a filter paper and a Buchner funnel. The crude product was then washed with acetone (1 L) and washed again with hot water (2 L). The product (520 g, yield: ca. 87%) was then air dried over night at room temperature and then was dried in a vacuum oven 150° C. for 4 to 6 hours. The product was a pale tan solid.

Figure 3:
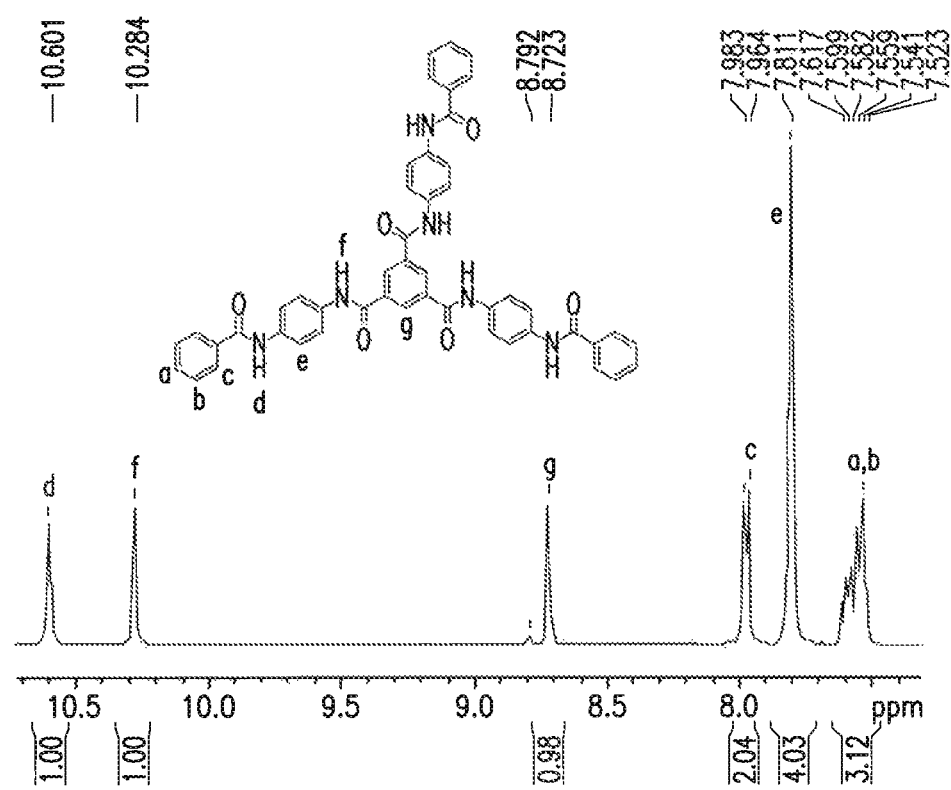
FIG. 3 is the Proton NMR characterization for N1,N3,N5-tris(4-benzamidophenyl)benzene-1,3,5-tricarboxamide (Compound C).

The Proton NMR characterization for the compound is shown in FIG. 3.

Synthesis of N1,N3,N5-tris(3-benzamidophenyl) benzene-1,3,5-tricarboxamide Compound D The synthesis of Compound D from trimesoyl chloride, benzoyl chloride and 1,3-phenylene diamine can be performed according to the following scheme:

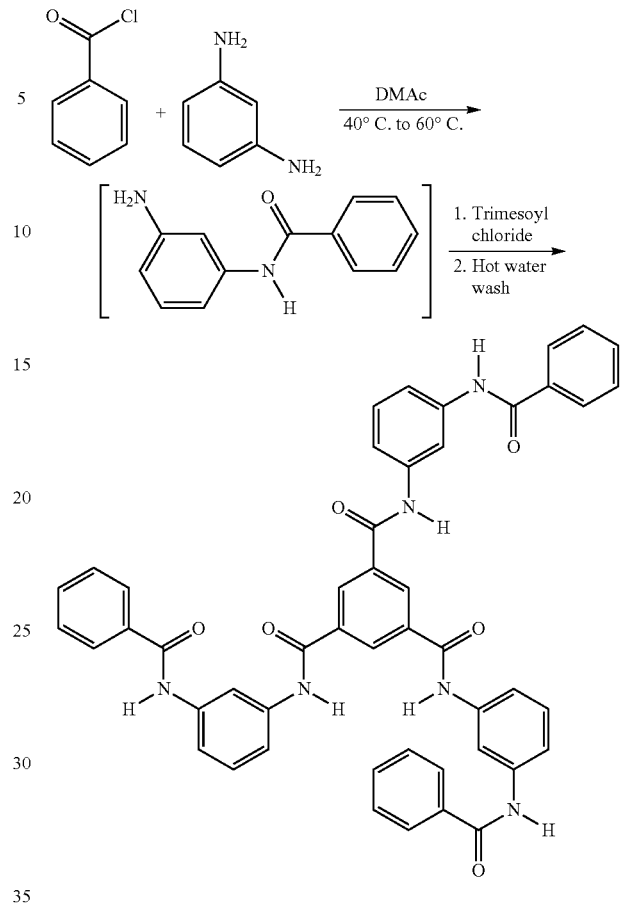

The experimental set up consisted of a 1 L glass beaker equipped with a glass rod stirrer coupled with an overhead mechanical stirrer. 1,3 phenylene diamine (20 g) was dissolved in warm dimethyl acetamide (200 mL) (alternatively N-methyl pyrrolidone can also be used) and maintained at 45° C. Next benzoyl chloride (26.51 g) was slowly added drop wise over a period of 1.5 to 2 hours, to the amine solution with constant stirring. The rate of addition of the benzoyl chloride was maintained such that the reaction temperature was maintained less than 60° C. After complete addition of the benzoyl chloride, the reaction mixture was gradually warmed to 85-90° C. and then allowed to cool to around 45-50° C. At this point, trimesoyl chloride (16.03 g) was gradually added to the reaction mixture such that the exotherm did not increase the reaction temperature above 60° C. After complete addition of the trimesoyl chloride, the reaction mixture was allowed to stir for additional 45 minutes, after which the reaction temperature was increased to 90° C. for about 30 minutes and then was cooled to room temperature. The mixture was allowed to rest overnight at room temperature. The product was recovered by precipitation through the addition of 1.5 L of distilled water, which was followed by was vacuum filtration using a filter paper and a Buchner funnel. The crude product was then washed with acetone (250 mL) and washed again with hot water (500 mL). The product (yield: ca. 90%) was then air dried over night at room temperature and then was dried in a vacuum oven 150° C. for 4 to 6 hours. The product was a pale tan solid. The Proton NMR characterization was as follows: $^1$H NMR (400 MHz $d_6$-DMSO): 10.68 (s, 3H, CONH), 10.3 (s, 3H, CONH), 8.74 (s, 3H, central Ar), 8.1

(d, 3H, m-phenylene Ar), 7.9 (d, 6H, ortho-ArH), 7.51 (m, 15H, meta-para-ArH and 6H, m-phenylene Ar) and 7.36 (m, 3H, m-phenylene Ar).

Example 1

Compounds A2, B2, and C were tested for their influence on the melt viscosity of a polymer that is commercially available from Ticona, LLC and has the following monomer content: 63% 4-hydroxybenzoic acid ("HBA"), 5% 2,6-hydroxynaphthoic acid ("HNA"), 16% terephthalic acid ("TA"), 11% 4,4'-biphenol ("BP"), and 5% acetaminophen ("APAP"). More particularly, the polymer was heated at 120° C. and powder coated with a pentaerythritol tetrastearate (PETS, commercial grade Lonza Glycolube P) at a 0.3 wt. % loading based on the weight of the polymer. The hot pellets were then coated with 2 wt. % (based on polymer weight) of one of Compounds A2, B2, or C. The mixtures were then melt mixed using a Leistritz 18 mm co-rotating fully intermeshing twin screw extruder having 6 temperature control zones (including at the extrusion die) and an overall LA) of 30. A general purpose screw design was used to compound the oligomers into a resin matrix. All materials were fed to the feed throat in the first barrel by means of a volumetric feeder. Materials were melted and mixed then extruded through a single hole strand die. Material was then quenched in a water bath to solidify and granulated in a pelletizer. The resultant pellets were then dried for 3 hours at 120° C. and scanning shear capillary melt viscosity measurements were carried out at 350° C. The results are set forth below.

| Comp. | Control | Polymer + Compound A2 | Polymer + Compound B2 | Polymer + Compound C |
|---|---|---|---|---|
| Melt Viscosity (1000 s$^{-1}$) (Pa-s) | 25.3 | 8.8 | 5.7 | 3.7 |
| Melt Viscosity (400 s$^{-1}$) (Pa-s) | 33.3 | 10.9 | 8.8 | 5.0 |
| Intrinsic Visc. (dL/g) | 6.96 | 6.40 | 5.50 | 5.43 |
| Tm (° C.) | 336.4 | 329.2 | 322.5 | 329.0 |
| Tc (° C.) | 289.3 | 288 | 283.72 | 290.0 |

As indicated, a melt viscosity reduction was achieved by the compounds of the present invention. To determine if this resulted in a change in the mechanical properties, the pellets were also injection molded to obtain specimen samples for tensile, impact, flexural and heat distortion temperature measurements. The results are set forth below.

| Comp. | Control | Polymer + Compound A2 | Polymer + Compound B2 | Polymer + Compound C |
|---|---|---|---|---|
| Flexural Modulus (MPa) | 12,500 | 11,000 | 11,300 | — |
| Flexural Break Stress (MPa) | 167 | 151 | 143 | — |
| Flexural Break Strain (%) | 3.4 | 3.3 | 2.7 | — |
| Tensile Modulus (MPa) | 13,150 | 10,550 | 11,800 | 13,400 |
| Tensile Break Stress (MPa) | 152 | 146 | 147 | 146 |
| Tensile Break Strain (%) | 1.74 | 2.18 | 1.86 | 1.65 |
| Charpy Notched (kJ/m) | 90.9 | 75.7 | 65.3 | 65.6 |

As indicated, only a small change in the mechanical properties was observed for the compositions. Without intending to be limited by theory, it is believed that a significant reduction in mechanical properties did not occur because the compounds did not react directly with the polymer backbone to reduce its molecular weight.

Example 2

A first sample (Sample 1) was formed. A 2 L flask was charged with 4-hydroxybenzoic acid (415.7 g), 2,6-hydroxynaphthoic acid (32 g), terephthalic acid (151.2 g), 4,4'-biphenol (122.9 g), acetominophen (37.8 g), and 50 mg of potassium acetate. The flask was equipped with C-shaped stirrer, a thermal couple, a gas inlet, and distillation head. The flask was placed under a low nitrogen purge and acetic anhydride (99.7% assay, 497.6 g) was added. The milky-white slurry was agitated at 75 rpm and heated to 140° C. over the course of 95 minutes using a fluidized sand bath. After this time, the mixture was then gradually heated to 360° C. steadily over 300 minutes. Reflux was seen once the reaction exceeded 140° C. and the overhead temperature increased to approximately 115° C. as acetic acid byproduct was removed from the system. During the heating, the mixture grew yellow and slightly more viscous and the vapor temperature gradually dropped to 90° C. Once the mixture had reached 360° C., the nitrogen flow was stopped. The flask was evacuated below 20 psi and the agitation slowed to 30 rpm over the course of 45 minutes. As the time under vacuum progressed, the mixture grew viscous. After 72 minutes, the final viscosity target was reached as gauged by the strain on the agitator motor (torque value of 30 units). The reaction was then stopped by releasing the vacuum and stopping the heat flow to the reactor. The flask was cooled and then polymer (Sample 1) was recovered as a solid, dense yellow-brown plug. Sample for analytical testing was obtained by mechanical size reduction.

A second sample (Sample 2) was formed as described for Sample 1, except that 18.7 grams of Compound C was also introduced into the reactor. It was observed that there were fewer residues in the distillate as compared to Sample 1. The reaction was stopped after 72 minutes—a torque value of 50 units was observed on the agitator motor.

The thermal properties of the melt polymerized polymers Sample 1 and Sample 2 were tested as described above. The results are set forth below in the following table.

| Sample | Additive | Tm (° C.) | Tc (° C.) | IV (dL/g) | MV at 1000 s$^{-1}$ (Pa * s) | MV at 400 s$^{-1}$ (Pa * s) |
|---|---|---|---|---|---|---|
| 1 | — | 361.6 | 301.8 | 8.4 | 75.7 | 118.2 |
| 2 | C | 343.0 | 284.7 | 5.0 | 137.8 | 230.1 |

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A polymer composition comprising a polymer and an aromatic amide compound having the following general formula (I):

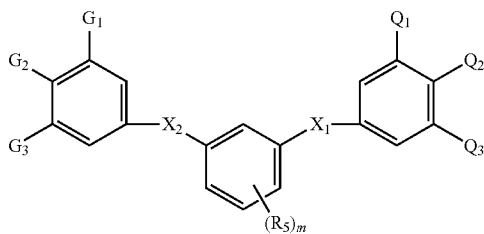

wherein,

X$_1$ and X$_2$ are independently C(O)HN or NHC(O);

G$_1$, G$_2$ and G$_3$ are independently hydrogen, C(O)HN-phenyl, or NHC(O)-phenyl, wherein at least one of G$_1$, G$_2$ and G$_3$ is C(O)HN-phenyl or NHC(O)-phenyl;

Q$_1$, Q$_2$, and Q$_3$ are independently hydrogen, C(O)HN-phenyl, or NHC(O)-phenyl, wherein at least one of Q$_1$, Q$_2$, and Q$_3$ is C(O)HN-phenyl or NHC(O)-phenyl;

R$_5$ is halo, haloalkyl, alkyl, alkenyl, aryl, heteroaryl, cycloalkyl, or heterocyclyl; and m is from 0 to 4.

2. The polymer composition of claim 1, wherein m is 0.

3. The polymer composition of claim 2, wherein the compound has the following general formula (II):

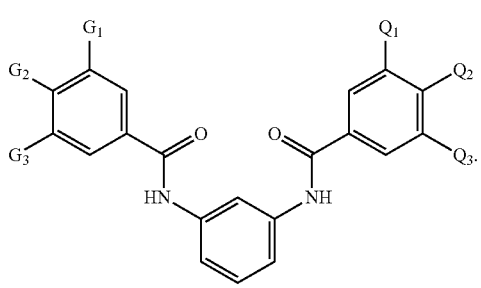

4. The polymer composition of claim 3, wherein G$_3$ and Q$_3$ are hydrogen.

5. The polymer composition of claim 4, wherein G$_1$ and Q$_1$ are hydrogen and G$_2$ and Q$_2$ selected from C(O)NH-phenyl or NHC(O)-phenyl.

6. The polymer composition of claim 4, wherein G$_2$ and Q$_2$ are hydrogen and G$_1$ and Q$_1$ are selected from C(O)NH-phenyl or NHC(O)-phenyl.

7. The polymer composition of claim 1, wherein the compound is provided by general formula (III):

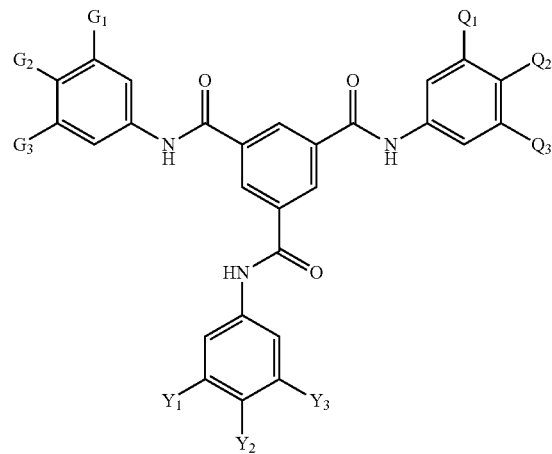

wherein,

Y$_1$, Y$_2$, and Y$_3$ are independently hydrogen, C(O)HN-phenyl, or NHC(O)-phenyl, and wherein at least one of Y$_1$, Y$_2$, and Y$_3$ is C(O)HN-phenyl or NHC(O)-phenyl.

8. The polymer composition of claim 7, wherein Y$_3$, G$_3$ and Q$_3$ are hydrogen.

9. The polymer composition of claim 8, wherein Y$_1$, G$_1$, and Q$_1$ are hydrogen and Y$_2$, G$_2$ and Q$_2$ are selected from C(O)NH-phenyl or NHC(O)-phenyl.

10. The polymer composition of claim 8, wherein Y$_2$, G$_2$ and Q$_2$ are hydrogen and Y$_1$, G$_1$ and Q$_1$ are selected from C(O)NH-phenyl or NHC(O)-phenyl.

11. The polymer composition of claim 1, wherein the compound is selected from the group consisting of the following compounds and combinations thereof:

| Structure | Name |
|---|---|
| 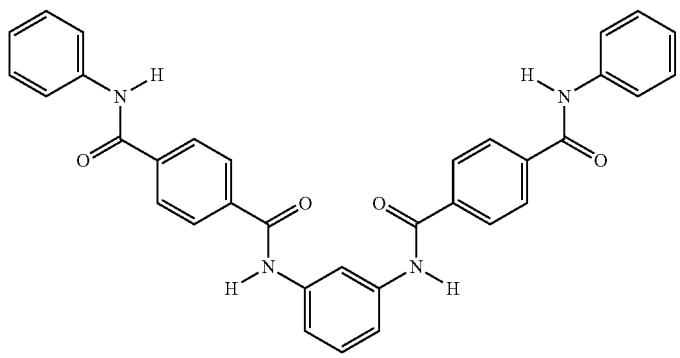 [SMILES: O=C(Nc1ccccc1)c1ccc(C(=O)Nc2cccc(NC(=O)c3ccc(C(=O)Nc4ccccc4)cc3)c2)cc1] | N4-phenyl-N1-[3-[[4-(phenylcarbamoyl)-benzoyl]amino]phenyl]terephthalamide |

| Structure | Name |
|---|---|
| 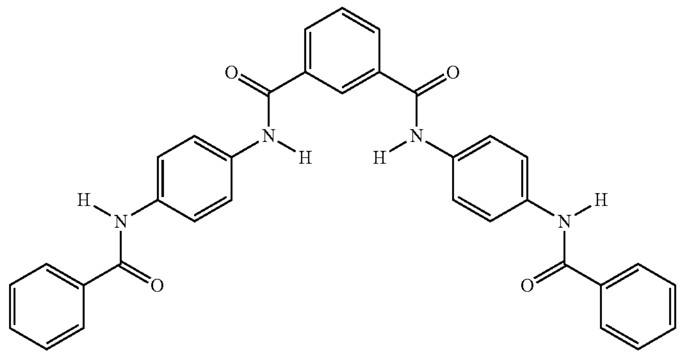 [SMILES: O=C(Nc1ccc(NC(=O)c2cccc(C(=O)Nc3ccc(NC(=O)c4ccccc4)cc3)c2)cc1)c1ccccc1] | N1,N3-bis(4-benzamidophenyl)benzene-1,3-dicarboxamide |
| 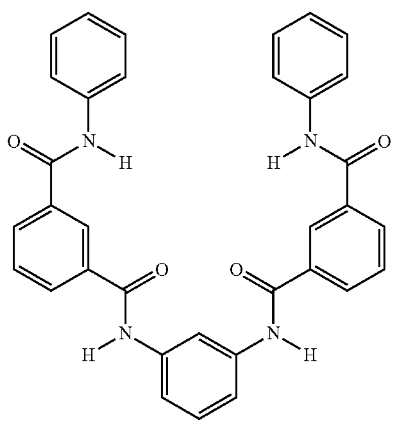 [SMILES: O=C(Nc1ccccc1)c1cccc(C(=O)Nc2cccc(NC(=O)c3cccc(C(=O)Nc4ccccc4)c3)c2)c1] | N3-phenyl-N1-[3-[[3-(phenylcarbamoyl)benzoyl]-amino]phenyl]benzene-1,3-dicarboxamide |
| 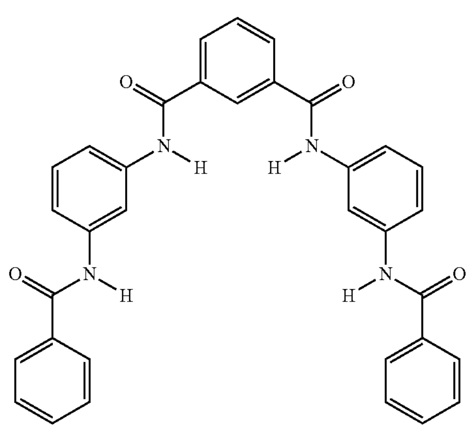 [SMILES: O=C(Nc1cccc(NC(=O)c2cccc(C(=O)Nc3cccc(NC(=O)c4ccccc4)c3)c2)c1)c1ccccc1] | N1,N3-bis(3-benzamidophenyl)benzene-1,3-dicarboxamide |

| Structure | Name |
|---|---|
| 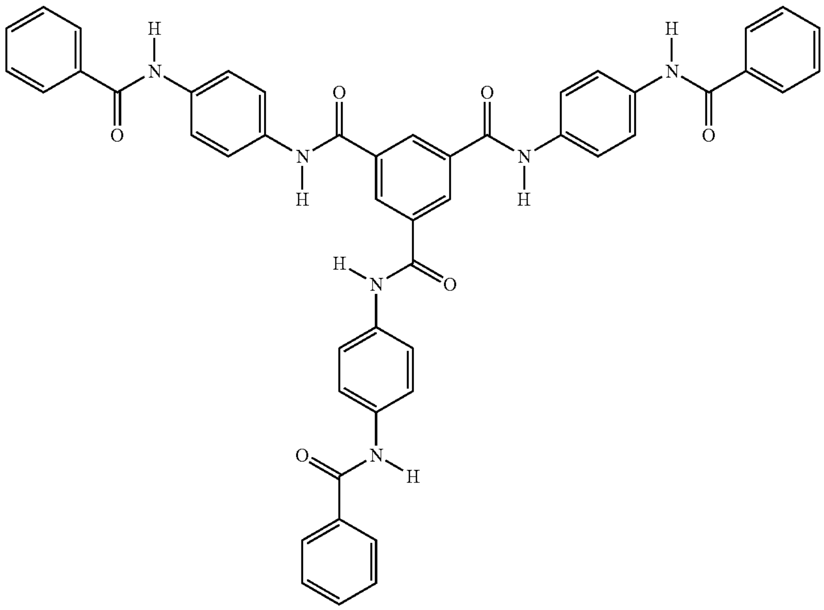 [SMILES: O=C(Nc1ccc(NC(=O)c2cc(C(=O)Nc3ccc(NC(=O)c4ccccc4)cc3)cc(C(=O)Nc3ccc(NC(=O)c4ccccc4)cc3)c2)cc1)c1ccccc1] | N1,N3,N5-tris(4-benzamidophenyl)benzene-1,3,5-tricarboxamide |
| 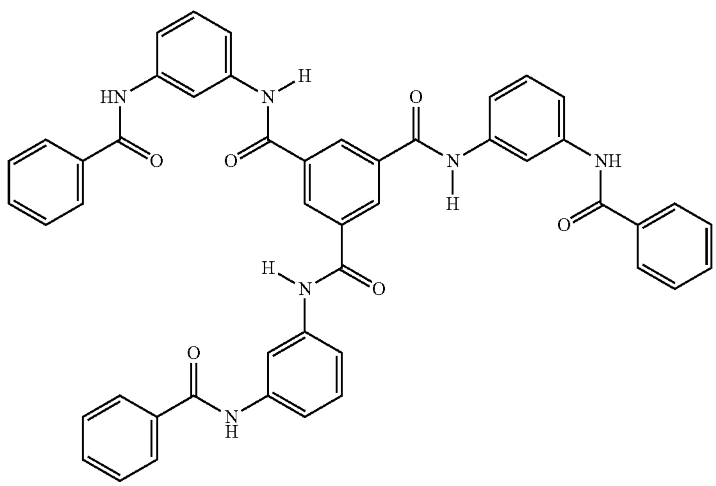 [SMILES: O=C(Nc1cccc(NC(=O)c2cc(C(=O)Nc3cccc(NC(=O)c4ccccc4)c3)cc(C(=O)Nc3cccc(NC(=O)c4ccccc4)c3)c2)c1)c1ccccc1] | N1,N3,N5-tris(3-benzamidophenyl)benzene-1,3,5-tricarboxamide |

12. The polymer composition of claim 1, wherein the compound is N1,N3-bis(4-benzamidophenyl)benzene-1,3-dicarboxamide or N1,N3-bis(3-benzamidophenyl)benzene-1,3-dicarboxamide.

13. The polymer composition of claim 1, wherein the compound is N1,N3,N5-tris(4-benzamidophenyl)benzene-1,3,5-tricarboxamide.

14. The polymer composition of claim 1, wherein the polymer is a thermotropic liquid crystalline polymer.

15. The polymer composition of claim 14, wherein the polymer is a wholly aromatic liquid crystalline polymer.

* * * * *